United States Patent
Jaen et al.

(10) Patent No.: US 6,727,267 B2
(45) Date of Patent: Apr. 27, 2004

(54) NS5B HVC POLYMERASE INHIBITORS

(75) Inventors: Juan C. Jaen, Burlingame, CA (US); Jay P. Powers, Pacifica, CA (US)

(73) Assignee: Tularik Inc., So. San Francisco, CA (US)

( * ) Notice: Subject to any disclaimer, the term of this patent is extended or adjusted under 35 U.S.C. 154(b) by 0 days.

(21) Appl. No.: 09/828,270

(22) Filed: Apr. 5, 2001

(65) Prior Publication Data

US 2002/0142290 A1 Oct. 3, 2002

Related U.S. Application Data

(60) Provisional application No. 60/194,912, filed on Apr. 5, 2001.

(51) Int. Cl.$^7$ .................. C07D 277/154; A61K 31/426
(52) U.S. Cl. ........................................ 514/369; 548/183
(58) Field of Search ........................... 548/183; 514/369

(56) References Cited

FOREIGN PATENT DOCUMENTS

| EP | 600717 A1 | * | 6/1994 | ......... C07D/207/08 |
|----|-----------|---|--------|----------------------|
| WO | WO 00 06529 | | 2/2000 | |
| WO | WO 00 10573 | | 3/2000 | |

OTHER PUBLICATIONS

Chemical Abstracts, vol. 120, No.1, Jan. 3, 1994, Columbus, Ohio, US; abstract No. 8507n.
Chemical Abstracts, vol. 68, No.7, Feb. 12, 1968, Columbus, Ohio, US; abstract No. 29633y.
Chemical Abstracts, vol. 77, No.19, Nov. 6, 1972, Columbus, Ohio, US; abstract No. 126531g.
Chemical Abstracts, vol. 54, No.4, Feb. 25, 1960, Columbus, Ohio, US; abstract No. 3383g.
Database Chemcats 'Online! Chemical Abstracts Service, Columbus, Ohio, Us; XP002180559 Order No. NS22748, Sep. 18, 2000.
Database Chemcats 'Online! Chemicals Abstracts Service, Columbus, Ohio, Us; XP002180557 Order Nos. T3258244, T3267912, T3267911,T3267910, T3267905, T3267904, T3267903, T3267901; T3267900, T3267899, T3267898, T3267767, T3196515, T3056249, T3056248, T3056247, T3056246, T3056245, T3056244, T3054351, T3054311, T3054310, T3054309, T3054308, T3054307, T3054306, T3054305, T3054304, T3054303, T3054302, T3054301, T3054300, Feb. 19, 2001.
Database Chemcats 'Online! Chemicals Abstracts Service, Columbus, Ohio, Us; XP002180558 Order No. ST218837, Feb. 12, 2001.

* cited by examiner

*Primary Examiner*—Robert Gerstl
(74) *Attorney, Agent, or Firm*—Townsend and Townsend and Crew LLP

(57) ABSTRACT

Compounds, compositions and methods are provided that are useful in the treatment and prevention of certain viral infections and associated diseases. In particular, the compounds of the invention inhibit the activity of a viral RNA polymerase. The subject methods are particularly useful in the treatment of diseases causes by hepatitis C virus infection.

4 Claims, 20 Drawing Sheets

General structure

General structure

FIGURE 2A

| Identifer | NS5b IC$_{50}$ (uM) | Benzylidene (R$_4$) | Amino substituent (R) | R$_5$ |
|---|---|---|---|---|
| 9 | ++ | 4-Cl-phenyl | phenylsulfonyl | H |
| 10 | ++ | phenyl | phenylsulfonyl | H |
| 11 | ++ | 4-methylphenyl | phenylsulfonyl | H |
| 12 | ++ | 4-NO$_2$-phenyl | phenylsulfonyl | H |
| 2 | ++ | 4-F-phenyl | phenylsulfonyl | H |
| 13 | ++ | 4-CF$_3$-phenyl | phenylsulfonyl | H |
| 14 | ++ | 4-(SCF$_3$)-phenyl | phenylsulfonyl | H |

| Identifer | NS5b IC₅₀ (uM) | Benzylidene (R₄) | Amino substituent (R) | R₅ |
|---|---|---|---|---|
| 15 | ++ | 3,4-dimethylphenyl | phenylsulfonyl | H |
| 16 | ++ | 2-naphthyl | phenylsulfonyl | H |
| 17 | ++ | 3-methyl-4-methoxyphenyl | phenylsulfonyl | H |
| 18 | ++ | 3-nitro-4-chlorophenyl | phenylsulfonyl | H |
| 19 | ++ | 3-fluoro-4-chlorophenyl | phenylsulfonyl | H |
| 20 | ++ | 3,4-dichlorophenyl | phenylsulfonyl | H |
| 21 | ++ | 2-fluorophenyl | phenylsulfonyl | H |

| Identifer | NS5b IC$_{50}$ (uM) | Benzylidene (R$_4$) | Amino substituent (R) | R$_5$ |
|---|---|---|---|---|
| 22 | ++ |  |  | H |
| 23 | ++ |  |  | H |
| 24 | ++ |  |  | H |
| 25 | ++ |  |  | H |
| 26 | ++ |  |  | H |
| 27 | ++ |  |  | H |
| 28 | ++ |  |  | H |

FIGURE 2E

| Identifer | NS5b IC$_{50}$ (uM) | Benzylidene (R$_4$) | Amino substituent (R) | R$_5$ |
|---|---|---|---|---|
| 35 | ++ | 3,4-dichlorophenyl | phenylsulfonyl | CH$_3$ |
| 36 | ++ | 1-methylimidazol-2-yl | phenylsulfonyl | H |
| 37 | ++ | 2,2-difluorobenzo[1,3]dioxol-5-yl | phenylsulfonyl | H |
| 38 | ++ | 2,3,4-trifluorophenyl | phenylsulfonyl | H |
| 39 | ++ | 2,4-difluorophenyl | phenylsulfonyl | H |
| 40 | ++ | 2,5-difluorophenyl | phenylsulfonyl | H |
| 41 | ++ | 2-fluoro-5-bromophenyl | phenylsulfonyl | H |

FIGURE 2G

| Identifer | NS5b IC$_{50}$ (uM) | Benzylidene (R$_4$) | Amino substituent (R) | R$_5$ |
|---|---|---|---|---|
| 49 | ++ | 3-CN-phenyl | phenylsulfonyl | H |
| 50 | ++ | 3-O⁻, 4-OMe, 5-Br-phenyl | phenylsulfonyl | H |
| 51 | ++ | 3-Br, 4-F-phenyl | phenylsulfonyl | H |
| 52 | ++ | 4-Br-phenyl | phenylsulfonyl | H |
| 53 | ++ | 4-OMe-phenyl | phenylsulfonyl | H |
| 54 | ++ | 2-Cl, 6-F-phenyl | phenylsulfonyl | H |
| 55 | ++ | 3,4,5-triF-phenyl | phenylsulfonyl | H |

FIGURE 2H

| Identifer | NS5b IC$_{50}$ (uM) | Benzylidene (R$_4$) | Amino substituent (R) | R$_5$ |
|---|---|---|---|---|
| 56 | ++ | benzo[1,3]dioxol-5-yl | phenylsulfonyl | H |
| 57 | + | 3,4-dimethoxyphenyl | phenylsulfonyl | H |
| 58 | ++ | 3-hydroxy-4-nitrophenyl | phenylsulfonyl | H |
| 59 | ++ | 3-methylphenyl | phenylsulfonyl | H |
| 60 | + | 6-methylpyridin-2-yl | phenylsulfonyl | H |
| 61 | ++ | 3,4-dichlorophenyl | 4-fluorophenylsulfonyl | H |
| 62 | ++ | 3,4-dibromophenyl | 3-chlorophenylsulfonyl | H |

FIGURE 2I

| Identifer | NS5b IC$_{50}$ (uM) | Benzylidene (R$_4$) | Amino substituent (R) | R$_5$ |
|---|---|---|---|---|
| 63 | ++ | 3,4-diCl-phenyl | -SO$_2$-(2,5-dimethylphenyl) | H |
| 3 | ++ | 3,4-diCl-phenyl | -SO$_2$-CH$_3$ | H |
| 64 | ++ | 3,4-diCl-phenyl | -CH$_3$ | H |
| 65 | ++ | 2,4,5-triF-phenyl | -SO$_2$-CH$_3$ | H |
| 66 | ++ | 3,4-diCl-phenyl | -SO$_2$-(2-Cl-phenyl) | H |
| 67 | ++ | 3,4-diBr-phenyl | -SO$_2$-(2-Cl-phenyl) | H |
| 68 | ++ | 3,4-diCl-phenyl | -SO$_2$-(3,5-diCl-phenyl) | H |
| 69 | ++ | 3,4-diBr-phenyl | -SO$_2$-(4-F-phenyl) | H |

FIGURE 2J

| Identifer | NS5b IC₅₀ (uM) | Benzylidene (R₄) | Amino substituent (R) | R₅ |
|---|---|---|---|---|
| 70 | + | pyrrole (2-pyrrolyl) | phenylsulfonyl | H |
| 71 | ++ | 5-(2-chloro-5-trifluoromethylphenyl)furan-2-yl | phenylsulfonyl | H |
| 72 | ++ | 2-methyl-2-phenylethenyl | phenylsulfonyl | H |
| 73 | ++ | 3,4-dichlorophenyl | 2-thienylsulfonyl | H |
| 74 | ++ | 3,4-dichlorophenyl | 2-fluorophenylsulfonyl | H |
| 75 | ++ | 3,4-dichlorophenyl | n-butylsulfonyl | H |
| 76 | ++ | fluoren-2-yl | phenylsulfonyl | H |

FIGURE 2K

| Identifer | NS5b IC$_{50}$ (uM) | Benzylidene (R$_4$) | Amino substituent (R) | R$_5$ |
|---|---|---|---|---|
| 77 | ++ | 3,4-dichlorophenyl | 3-nitrophenylsulfonyl | H |
| 78 | ++ | 2,4,5-trifluorophenyl | benzylsulfonyl | H |
| 79 | ++ | 2,4,5-trifluorophenyl | benzyl | H |
| 80 | ++ | 3,4-dichlorophenyl | methoxycarbonylmethyl | H |
| 81 | ++ | 3,4-dichlorophenyl | isopropylsulfonyl | H |
| 82 | ++ | 4-styrylphenyl | 3-nitrophenylsulfonyl | H |

FIGURE 2L

| Identifer | NS5b IC$_{50}$ (uM) | Structure |
|---|---|---|
| 83 | ++ | 3,4-dichlorobenzylidene-2-thioxo-thiazolidin-4-one with N-methyl-N-benzoyl substituent |
| 6 | ++ | 3,4-dichlorobenzylidene-2-thioxo-thiazolidin-4-one with N-(4-chlorophenylsulfonyl) |
| 7 | ++ | 3,4-dichlorobenzylidene-2-methyl-thiazolidin-4-one with N-(4-fluorophenylsulfonyl) |
| 84 | ++ | 5-(3,4-dichlorobenzyl)-2-thioxo-thiazolidin-4-one with N-NH-phenylsulfonyl |
| 85 | ++ | 5-(3,4-dichlorobenzyl)-4-hydroxy-2-thioxo-thiazolidine with N-NH-phenylsulfonyl |
| 86 | ++ | 5-[(3,4-dibromophenyl)(hydroxy)methyl]-2-thioxo-thiazolidin-4-one with N-NH-(4-bromophenylsulfonyl) |

| Identifer | NS5b IC$_{50}$ (uM) | Benzylidene (R$_4$) | R | Y | X | R$_5$ |
|---|---|---|---|---|---|---|
| 87 | ++ | 4-NO$_2$-phenyl | NH$_2$ | S | S | H |
| 88 | ++ | 4-F-phenyl | NH$_2$ | S | S | H |
| 89 | ++ | 4-CN-phenyl | NH$_2$ | S | S | H |
| 1 | ++ | 4-Cl-phenyl | NH$_2$ | S | S | H |
| 90 | + | phenyl | NH$_2$ | S | S | H |
| 91 | + | 4-N(CH$_3$)$_2$-phenyl | NH$_2$ | S | S | H |
| 92 | + | 4-OCH$_3$-phenyl | NH$_2$ | S | S | H |

| Identifer | NS5b IC$_{50}$ (uM) | Benzylidene (R$_4$) | R | Y | X | R$_5$ |
|---|---|---|---|---|---|---|
| 93 | + | 4-OC$_6$H$_6$-phenyl | NH$_2$ | S | S | H |
| 94 | ++ | 2,4,5-trifluorophenyl | NH$_2$ | S | S | H |
| 95 | ++ | 3,4-dichlorophenyl | H | S | S | H |
| 96 | ++ | 2-chlorophenyl | H | S | S | H |
| 97 | + | 4-chlorophenyl | H | S | S | H |
| 98 | + | 4-chlorophenyl | H | O | S | H |
| 99 | ++ | 4-nitrophenyl | CH$_3$ | S | S | H |

| Identifer | NS5b IC$_{50}$ (uM) | Benzylidene (R$_4$) | R | Y | X | R$_5$ |
|---|---|---|---|---|---|---|
| 100 | + |  3,4-diCl-phenyl | CH$_3$ | S | S | H |
| 101 | ++ |  4-NO$_2$-phenyl | H | S | S | H |
| 102 | + |  4-Cl-phenyl | Bn | S | S | H |
| 103 | + | 4-Cl-phenyl | Et | S | S | H |
| 104 | + | 4-Cl-phenyl | CH$_3$ | S | S | H |
| 105 | + |  4-OMe-phenyl | Bn | S | S | H |
| 106 | + |  4-Me-phenyl | Bn | S | S | H |

| Identifer | NS5b IC$_{50}$ (uM) | Benzylidene (R$_4$) | R | Y | X | R$_5$ |
|---|---|---|---|---|---|---|
| 107 | ++ | furan-2-yl | H | S | S | H |
| 108 | ++ | 3,4-dimethylfuran-2-yl | H | S | S | H |
| 109 | ++ | 2-methoxy-4-hydroxyphenyl | H | S | S | H |
| 110 | ++ | 4-bromophenyl | H | S | S | H |
| 111 | ++ | 5-(3-chlorophenyl)furan-2-yl | H | S | S | H |
| 112 | + | 5-(2,5-dichlorophenyl)furan-2-yl | H | S | S | H |
| 113 | ++ | 5-(2,3-dichlorophenyl)furan-2-yl | H | S | S | H |

| Identifer | NS5b IC$_{50}$ (uM) | Benzylidene (R$_4$) | R | Y | X | R$_5$ |
|---|---|---|---|---|---|---|
| 114 | ++ | thiophene-4-methoxyphenyl | H | S | S | H |
| 115 | ++ | furan-(2-Cl-5-CF$_3$-phenyl) | H | S | S | H |
| 116 | ++ | furan-(2-Cl-5-CF$_3$-phenyl) | NH$_2$ | S | S | H |
| 117 | ++ | furan-(3-Cl-phenyl) | NH$_2$ | S | S | H |

NS5B HVC POLYMERASE INHIBITORS

CROSS-REFERENCES TO RELATED APPLICATIONS

This application claims priority to U.S. Provisional Application No. 60/194,912, filed Apr. 5, 2001, the disclosure of which is incorporated by reference herein.

BACKGROUND OF THE INVENTION

Hepatitis C virus (HCV) is considered to be the major etiological agent of non-A non-B (NANB) hepatitis, chronic liver disease, and hepatocellular carcinoma (HCC) around the world. The viral infection accounts for greater than 90% of transfusion-associated hepatitis in the U.S. and it is the predominant form of hepatitis in adults over 40 years of age. Almost all of the infections result in chronic hepatitis and nearly 20% of infected patients develop liver cirrhosis.

The virus particle has not been identified due to the lack of an efficient in vitro replication system and the extremely low amount of HCV particles in infected liver tissues or blood. However, molecular cloning of the viral genome has been accomplished by isolating the messenger RNA (mRNA) from the serum of infected chimpanzees then cloning using recombinant methodologies. See, Grakoui et al. (1993) *J. Virol.* 67:1385–1395. It is now known that HCV contains a positive strand RNA genome comprising approximately 9400 nucleotides, whose organization is similar to that of flaviviruses and pestiviruses. The genome of HCV, like that of flavi- and pestiviruses, encodes a single large polyprotein of about 3000 amino acids which undergoes proteolysis to form mature viral proteins in infected cells.

Cell-free translation of the viral polyprotein and cell culture expression studies have established that the HCV polyprotein is processed by cellular and viral proteases to produce the putative structural and nonstructural (NS) proteins. At least nine mature viral proteins are produced from the polyprotein by specific proteolysis. The order and nomenclature of the cleavage products are as follows: $NH_2$-C-E1-E2-NS2-NS3-NS4A-NS4B-NS5A-NS5B-COOH. The three amino terminal putative structural proteins, C (capsid), E1, and E2 (two envelope glycoproteins), are believed to be cleaved by host signal peptidases of the endoplasmic reticulum (ER). The host enzyme is also responsible for generating the amino terminus of NS2. The proteolytic processing of the nonstructural proteins is carried out by the viral proteases: NS2–3 and NS3, contained within the viral polyprotein.

The cleavages occurring at NS4A/4B, 4B/5A, 5A/5B sites occur in a trans enzymatic reaction. Additionally, experiments using transient expression of various forms of HCV NS polyproteins in mammalian cells have established that the NS3 serine protease is necessary but not sufficient for efficient processing of all these cleavages. Like flaviviruses, the HCV NS3 protease also requires a cofactor to catalyze some of these cleavage reactions. In addition to the serine protease NS3, the NS4A protein is absolutely required for the cleavage of the substrate at the NS3/4A and 4B/5A sites and increases the efficiency of cleavage of the substrate between 5A/5B, and possibly 4A/4B.

Each of these proteins is key to the viral replicase complex, enabling the virus to replicate its RNA genome and produce progeny viruses. Thus there is a need for the development of inhibitors of these proteins. The present invention provides compounds that are useful in inhibiting NS5B function through covalent modification of a cysteine residue in NS5B.

SUMMARY OF THE INVENTION

The present invention provides, inter alia, compounds, compositions and methods that are useful for treating viral infections and associated diseases, particularly HCV infections and associated diseases. The compounds of the invention inhibit viral replication, preferably HCV replication. The compounds are those of formulae I, II, III, IV, V, VI, and VIIa and VIIb, described in detail below.

The methods of the invention comprise administering to an infected or susceptible host a therapeutically or prophylactically effective amount of a compound of formulae I, II, III, IV, V, VI, and VIIa and VIIb, or a pharmaceutically acceptable salt or prodrug thereof.

DETAILED DESCRIPTION OF THE INVENTION

Abbreviations and Definitions

Figure 1A:
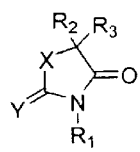
FIGS. 1A and 1B provide structures for a number of preferred embodiments.
Figure 1A:
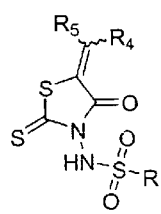
Figure 1A:
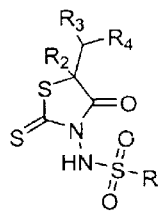
Figure 1A:
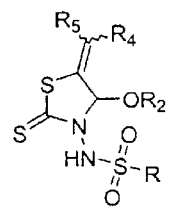
Figure 1A:
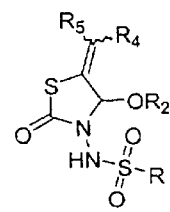
Figure 1A:
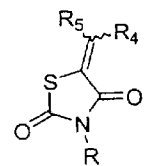
Figure 1A:
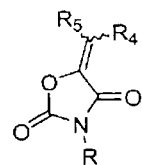
Figure 1A:
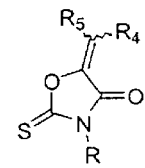
Figure 1A:
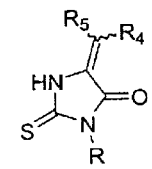
Figure 1A:
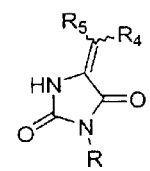
Figure 1A:
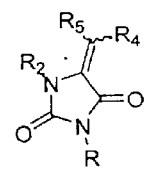
Figure 1A:
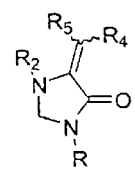
Figure 1A:
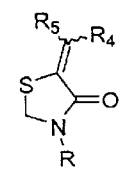
Figure 1A:
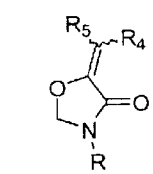
Figure 1A:
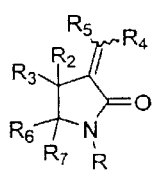
Figure 1A:
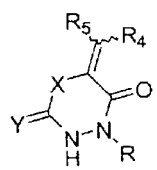
Figure 1A:
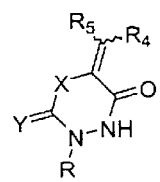
Figure 1B:
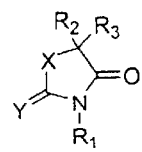
Figure 1B:
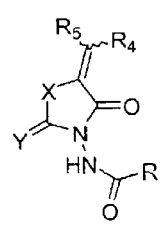
Figure 1B:
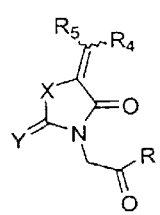
Figure 1B:
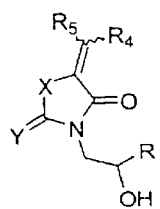
Figure 1B:
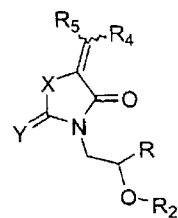
Figure 1B:
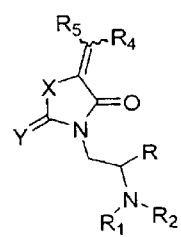
Figure 1B:
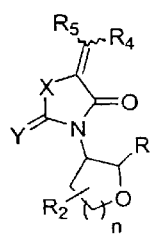
Figure 1B:
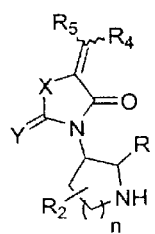
Figure 1B:
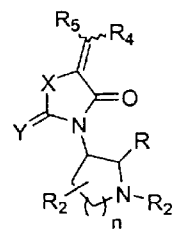
Figure 1B:
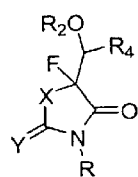
Figure 1B:
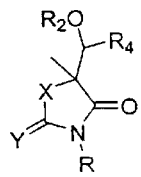
Figure 1B:
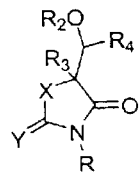
Figure 1B:
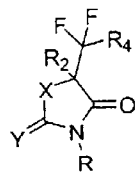
Figure 1B:
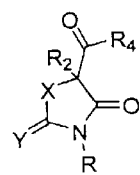
Figure 1B:
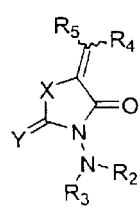
Figure 1B:
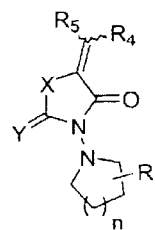
Figure 1B:
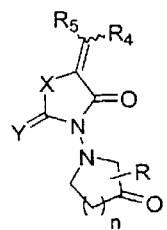
Figure 2B:
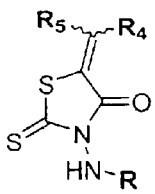
FIGS. 2A–2Q provide structures for a variety of compounds prepared as generally described herein.
Figure 2C:
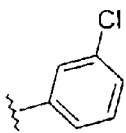
Figure 2C:
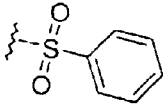
Figure 2C:
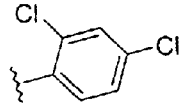
Figure 2C:
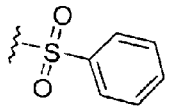
Figure 2C:
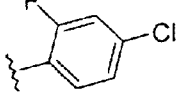
Figure 2C:
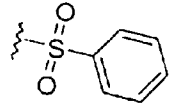
Figure 2C:
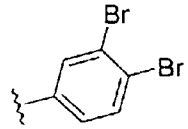
Figure 2C:
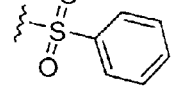
Figure 2C:
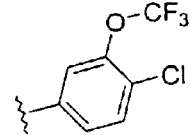
Figure 2C:
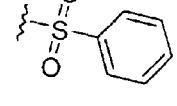
Figure 2C:
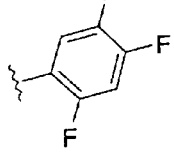
Figure 2C:
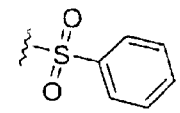
Figure 2C:
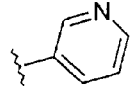
Figure 2C:
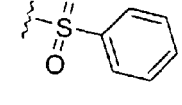
Figure 2D:
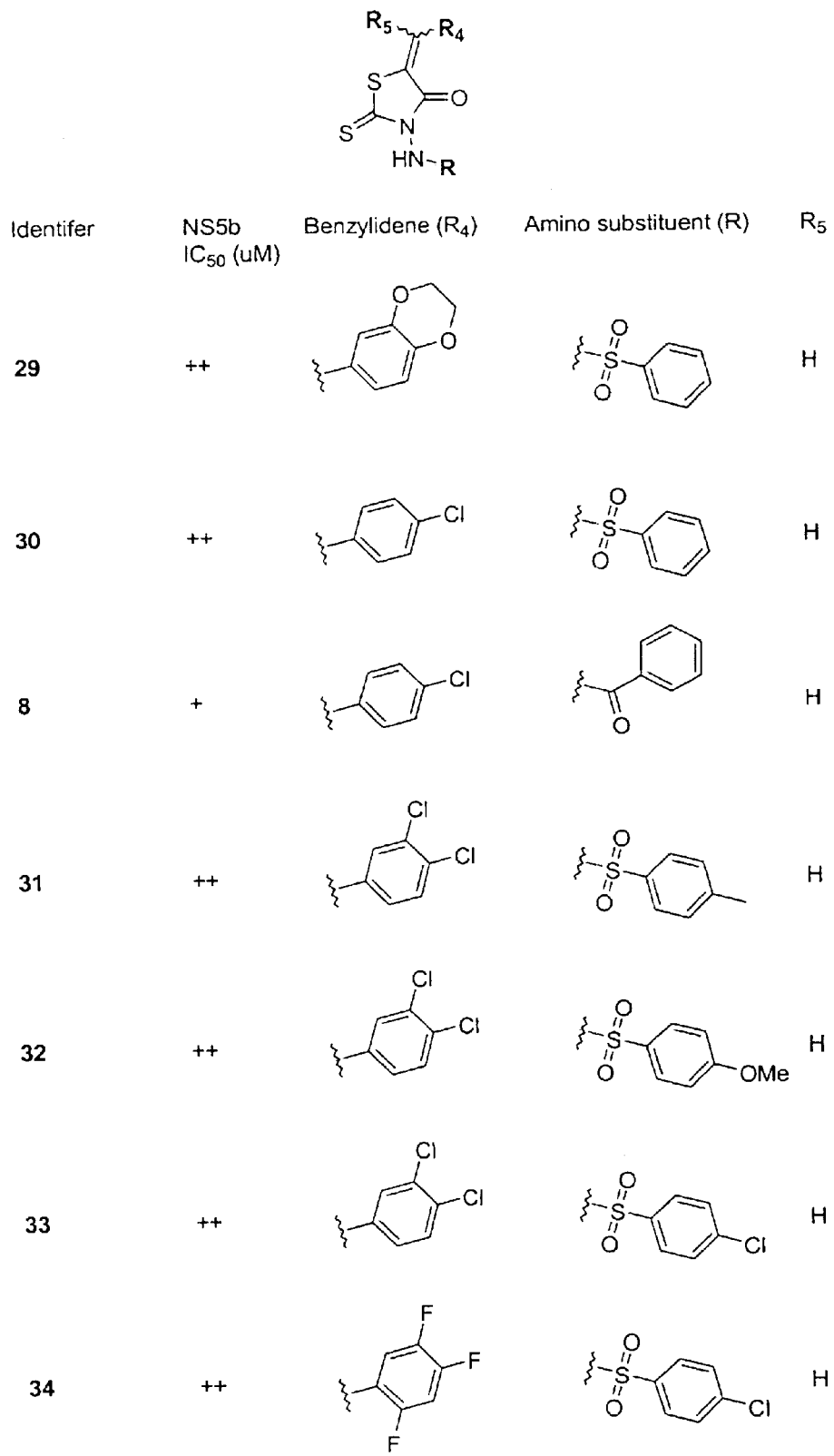
Figure 2F:
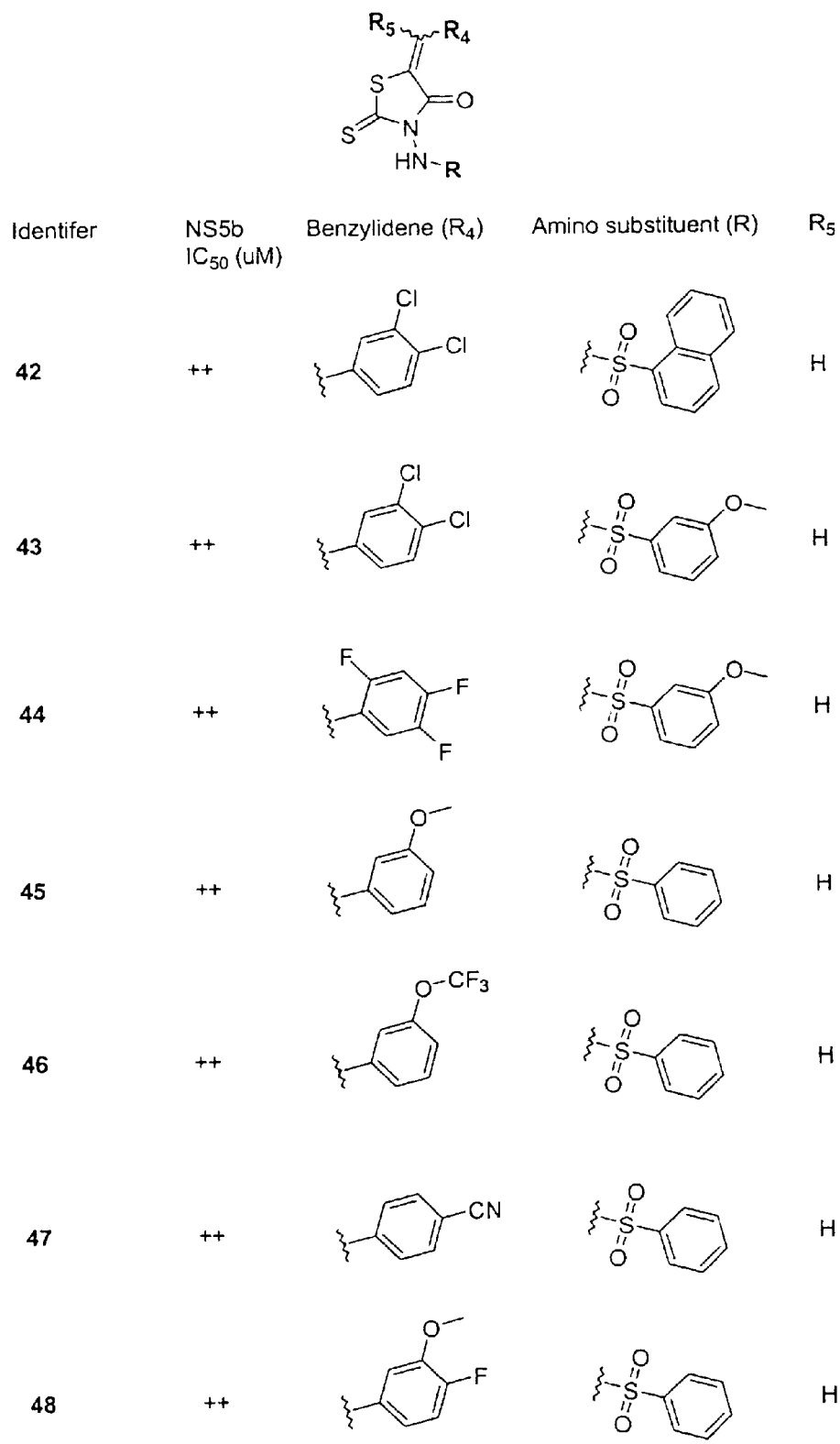
Figure 2M:
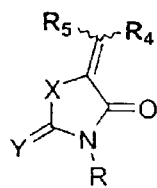
Figure 2N:
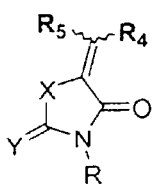
Figure 2O:
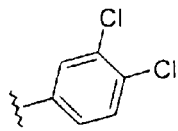
Figure 2O:
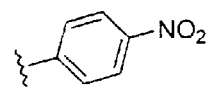
Figure 2O:
Figure 2O:
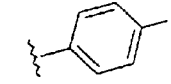
Figure 2O:
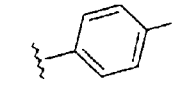
Figure 2O:
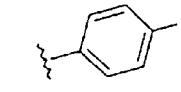
Figure 2P:
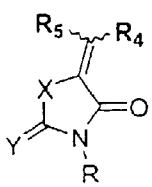
Figure 2Q:
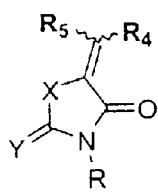

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of barring a subject from acquiring a disease. As used herein, "prevent", "preventing" and "prevention" also include reducing a subject's risk of acquiring a disease.

The term "therapeutically effective amount" refers to that amount of the compound being administered sufficient to prevent development of or alleviate to some extent one or more of the symptoms of the disease being treated.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

"Flaviviridae virus", as used herein, refers to a virus of the family Flaviviridae, which family includes the Flavivirus, Pestivirus and Hepacivirus or hepatitis C-like virus genera. Representative species of the genus Flavivirus include yellow fever virus, tick-borne encephalitis virus, Rio Bravo virus, Japanese encephalitis virus, Tyuleniy virus, Ntaya virus, Uganda S virus, Dengue virus and Modoc virus. Representative species of the genus Pestivirus include bovine diarrhea virus, border disease virus and hog cholera virus. A representative species of the genus of hepatitis C-like viruses is hepatitis C virus. Unassigned viruses in the family Flaviviridae are included in the meaning of Flaviviridae virus.

The term "physiological conditions", as used herein, refers to the normal, not pathological, functioning or state of a mammal or a tissue or organ of a mammal. Exemplary physiological conditions in humans include pH of about 7.35 to about 7.45, temperature of about 36.5° C. to about 37.4° C. and electrolytic balance, e.g., serum calcium of about 8.5 mg/dL to about 10.9 mg/dL.

The term "activated", as used herein, refers to a chemical bond or group having increased reactivity to nucleophilic attack relative to the unsubstituted bond or group. Activation includes, but is not limited to, activation by substitution and by coordination. For example, a nonaromatic bond or group may be activated by substitution with one or more electron withdrawing functional groups, such as nitro, sulfonate and carbonyl or a halogen, or by coordination to one or more metal groups or Lewis acids.

The terms "unactivated" and "deactivated", as used herein, refer to a chemical bond or group having decreased reactivity relative to the unsubstituted bond or group. Deactivation includes, but is not limited to, deactivation by substitution. For example, a nonaromatic bond or group may be activated by substitution with one or more electron donating functional groups, such as alkyl, amino, N-amido, hydroxy, alkoxy and acyloxy.

The term "electrophilic moiety" refers to a chemical group that is electron deficient and reactive with chemical groups having an excess of electrons, as commonly understood in the art. Exemplary electrophilic moieties include, but are not limited to, isothiocyanate, maleimide, haloacetamide, vinylsulfone, benzylic halide, electron-dificient aromatic rings, such as nitro-substituted pyrimidine rings, electron-deficient alkenes, such as $\alpha,\beta$-unsaturated carbonyls, carbonyl, alkyl halide, and the like.

The term "modulate" refers to the ability of a compound to increase or decrease the catalytic activity of a viral polymerase, e.g., a viral RNA polymerase. A modulator preferably activates the catalytic activity of a viral polymerase, more preferably activates or inhibits the catalytic activity of a viral polymerase, depending on the concentration of the compound exposed to the viral polymerase, or most preferably inhibits the catalytic activity of a viral polymerase.

The term "modify" refers to the act of altering, in whole or in part, the structure of a molecule, e.g., a protein. Modification may be covalent or noncovalent, and includes, but is not limited to, aggregation, association, substitution, conjugation and/or elimination of a chemical group. Modification may alter the function or other properties (e.g., chemical, physical) of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_8$ means one to eight carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkylene" by itself or as part of another substituent means a divalent radical derived from an alkane, as exemplified by —$CH_2CH_2CH_2CH_2$—. Typically, an alkyl or alkylene group will have from 1 to 24 carbon atoms, with those groups having 10 or fewer carbon atoms being preferred in the present invention. A "lower alkyl" or "lower alkylene" is a shorter chain alkyl or alkylene group, having eight or fewer carbon atoms.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2CH_2$—NH—$CH_2$—. For heteroalkylene groups, heteroatoms can also occupy either or both of the chain termini. Still further, for alkylene and heteroalkylene linking groups, no orientation of the linking group is implied.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

An "activated carbonyl" group is a carbonyl group whose electrophilicity is enhanced as a result of the groups attached to either side of the carbonyl. Examples of such activated carbonyl groups are (polyfluoroalkyl)ketones, (polyfluoroalkyl)aldehydes, alpha-keto esters, alpha-keto acids, alpha-keto amides, 1,2-diketones, 2-acylthiazoles, 2-acylimidazoles, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy) propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted (C$_1$–C$_8$)alkyl and heteroalkyl, unsubstituted aryl, aryl substituted with 1–3halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl, (unsubstituted aryl)-(C$_1$–C$_4$)alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3,and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) J. Pharm. Sci.66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

General

Viral polymerases are attractive targets for antiviral drug development. For example, inhibitors of Viral RNA polymerase activity have been described; see, for example, Altamura et al., WO 00/06529 and Bailey et al., WO 00/10573,which references are incorporated by reference herein.

The HCV protein NS5B is an RNA dependent RNA polymerase; see, e.g., Lohmann et al. (1997) *J. Virol.* 71:8416–8428,Behrens et al. (1996) *EMBO J.* 15:12–22 and Ishido et al. (1998) *Biochem. Biophys. Res. Commun.* 244:35–40, which references are incorporated by reference herein. HCV NS5B (EC 2.7.7.48) has the sequence shown in SEQ ID NO:1,which sequence corresponds to C-terminal residues 2420–3010 of HCV (GenBank Acc. No. NC_001433) (Kato et al. (1990) *Proc. Natl. Acad. Sci. U.S.A.* 87:9524–9528). NS5B contains sequence motifs that are highly conserved among all the RNA-dependent RNA polymerases characterized to date.

Compounds

The present invention provides compounds having antiviral activity. It is believed that the compounds of the invention will block viral replication by specifically inhibiting the activity of a viral polymerase. Viral RNA polymerase is required for the transcription of genomic RNA, which process is required for replication of the genome of an RNA virus. Therefore, inhibition of viral RNA polymerase will inhibit viral replication.

While a precise understanding of the mechanism by which compounds inhibit viral RNA polymerase activity is not required in order to practice the present invention, it is believed that the compounds interact with a cysteine residue of the NS5B protein, which mediates the RNA-dependent RNA polymerase (RdRp) activity of HCV. In particular, it is believed that the compounds covalently modify cysteine 366 ($Cys_{366}$) of HCV NS5B protein. $Cys_{366}$ of the NS5B sequence described herein corresponds to cysteine residue 2785 ($Cys_{2785}$) of the full-length HCV sequence, vide supra.

The compounds of the invention possess an electrophilic moiety that is capable of reacting with a thiol group. Specifically, the compounds of the invention bind covalently to $Cys_{366}$ of the NS5B protein, and this binding is specific. Compounds contemplated by the invention include, but are not limited to, the exemplary compounds provided herein. The skilled practitioner can propose additional compounds possessing an electrophilic moiety that will react with $Cys_{366}$ of the HCV NS5B protein or with a cysteine residue of a viral RdRp protein that corresponds to $Cys_{366}$ of HCV NS5B protein, i.e., a cysteine residue that is functionally similar to $Cys_{366}$ of HCV NS5B protein, in a similar manner.

A viral RdRp protein containing a cysteine residue that corresponds to $Cys_{366}$ of HCV NS5B protein may be identified by comparison of a viral RdRp protein sequence to the sequence disclosed herein using amino acid sequence alignment methods, as known in the art (Altschul et al. (1990) *J. Mol. Biol.* 215:403–410). See, for example, the methods described in Koonin et al. (1991) *J. Gen. Virol.* 72:2197–2206.Exemplary viral RNA-dependent RNA polymerases containing a cysteine residue that corresponds to $Cys_{366}$ of HCV NS5B protein include the RNA-dependent RNA polymerases of flaviviruses, pestiviruses, hepaciviruses, carmoviruses, tombusviruses and dianthoviruses.

The vast majority of the compounds contemplated for use in the present invention are novel, while some are available from commercial sources. It is to be understood that the invention includes those compounds that are novel, as well as pharmaceutical compositions, various methods (e.g., methods of treating or preventing certain viral infections), and the like which include both the novel compounds of the invention and compounds that are commercially available. Exemplary commercially available compounds include:

N-[4-oxo-5-(phenylmethylene)-2-thioxo-3-thazolidinyl] benzenesulfonamide (Otava) (10), N-[5-[(4-bromophenyl)methylene]-4-oxo-2-thioxo-3-thazolidinyl]benzenesulfonamide (Otava) (52), N-[5-[(4-chlorophenyl)methylene]-4-oxo-2-thioxo-3-thiazolidinyl]benzenesulfonamide (Otava) (9), N-[5-[(4-methoxyphenyl)methylene]-4-oxo-2-thioxo-3-thiazolidinyl]benzenesulfonamide (Otava) (53), N-[5-[(3,4-dimethoxyphenyl)methylene]-4-oxo-2-thioxo-3-thiazolidinyl]benzenesulfonamide (Otava) (57), 3-amino-5-(phenylmethylene)-2-thioxo-4-thiazolidinone (Nanosyn, Otava, AsInEx) (90), 3-amino-5-[(4-nitrophenyl)methylene]-2-thioxo-4-thiazolidinone (Nanosyn, Otava) (87) and 3-amino-5-[(4-methoxyphenyl)methylene]-2-thioxo-4-thiazolidinone (Otava, AsInEx, Sigma-Aldrich) (92).

In preferred embodiments the NS5B protein is from hepatitis C virus. In one group of embodiments the covalent bond is reversible under physiological conditions. In other embodiments, the covalent bond is irreversible under physiological conditions. More particularly, the covalent bond results from a reaction selected from the group consisting of a Michael addition of said cysteine residue to an activated double or triple bond in said compound, an aromatic or aliphatic nucleophilic substitution reaction of said cysteine residue with an electrophilic center in said compound, a thioester forming reaction between said cysteine residue and a carboxylic acid or carboxylic acid derivative in said compound, a disulfide forming reaction between said cysteine residue and a sulfur-containing group in said compound, and a hemi-thioketal forming reaction between said cysteine residue and an activated or unactivated carbonyl group in said compound.

In a first group of embodiments, the compounds useful for the covalent modification of a viral RNA-dependent RNA polymerase protein has the formula:

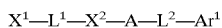

$$X^1—L^1—X^2—A—L^2—Ar^1$$

wherein

A is a electrophilic group that reacts with a cysteine residue of said protein;

$Ar^1$ is a member selected from the group consisting of substituted or unsubstituted aryl and substituted or unsubstituted heteroaryl;

$X^1$ is a member selected from the group consisting of —H, substituted or unsubstituted alkyl, substituted or unsubstituted aryl, substituted or unsubstituted heteroaryl, —CN, —CO₂H, —SO₃H, —C(O)NHOH, —NH₂, —OH, —NH(lower alkyl), —O(lower alkyl), —N(lower alkyl)₂, and —C(O)—NH(3-tetrazolyl);

$L^1$ is a divalent linking group selected from the group consisting of —CH₂CH₂—, —CH=CH—, —C≡C—, —O—, —S(O)ₙ—, —N(Rₐ)—, —C(O)—, —C(O)O—, —SO₂N(Rₐ)—, —CON(Rₐ)—, —N(Rₐ)CON(Rᵦ)—, —N(Rₐ)N(Rᵦ)—, —N(Rₐ)SO₂N(Rᵦ)—, —N(Rₐ)SO₂—, —N(Rₐ)—O—, =N—O—, lower alkylene, —O-lower alkylene, —S(O)ₙ-lower alkylene, N(Rₐ)-lower alkylene, —SO₂N(Rₐ)-lower alkylene, lower alkylene-SO₂N(Rₐ)—, —CON(Rₐ)-lower alkylene, lower alkylene-CON(Rₐ)—, —N(Rₐ)CON(Rᵦ)-lower alkylene, lower alkylene-N(Rₐ)N(Rᵦ)—, —N(Rₐ)SO₂N(Rᵦ)-lower alkylene, —N(Rₐ)—O-lower alkylene, lower alkylene-N(Rₐ)—O—, =N—O-lower alkylene, lower heteroalkylene, —O-lower heteroalkylene, —S(O)ₙ-lower heteroalkylene, N(Rₐ)-lower heteroalkylene, —SO₂N(Rₐ)-lower heteroalkylene, lower heteroalkylene-SO₂N(Rₐ)—, —CON(Rₐ)-lower heteroalkylene, lower heteroalkylene-CON(Rₐ)—, —N(Rₐ)CON(Rᵦ)-lower heteroalkylene, lower heteroalkylene-N(Rₐ)N(Rᵦ)—, —N(Rₐ)SO₂N(Rᵦ)-lower heteroalkylene, —N(Rₐ)—O-lower heteroalkylene, lower heteroalkylene-N(Rₐ)—O—, =N—O-lower alkylene, aryl and heteroaryl;

wherein Rₐ, Rᵦ, R_c, R_d, R_e and R_f are each members independently selected from the group consisting of H, lower alkyl, lower heteroalkyl, —C(O)-lower alkyl, —C(O)-lower heteroalkyl, —S(O)₂-lower alkyl, and —S(O)₂-lower heteroalkyl; the subscript n is an integer of from 0 to 2; the subscript m is an integer of from 0 to 3; and the bond between $X^2$ and A can be a single, double or triple bond, depending on the nature of $X^2$ and A;

$X^2$ is a member selected from the group consisting of substituted or unsubstituted aryl, substituted or unsubstituted heteroaryl, substituted or unsubstituted cycloalkyl, and substituted or unsubstituted heterocycloalkyl; and $L^2$ is a divalent linking group selected from the group consisting of —CH₂CH₂—, —(C(R_c)=C(R_d))_m—, —O—, —S(O)ₙ—, —N(R_e)—, —C(O)—, —C(O)O—, —SO₂N(R_e)—, —CON(R_e)—, —N(R_e)CON(R_f)—, —N(R_e)N(R_f)—, —N(R_e)SO₂N(R_f)—, —N(R_e)—O—, =N—O—, lower alkylene, perfluoro lower alkylene, polyfluoro lower alkylene, —O-lower alkylene, —S(O)ₙ-lower alkylene, N(R_e)-lower alkylene, —SO₂N(R_e)-lower alkylene, lower alkylene-SO₂N(R_e)—, —CON(R_e)-lower alkylene, lower alkylene-CON(R_e)—, —N(R_e)CON(R_f)-lower alkylene, lower alkylene-N(R_e)N(R_f)—, —N(R_e)SO₂N(R_f)-lower alkylene, —N(R_e)—O-lower alkylene, lower alkylene-N(R_e)—O—, =N—O-lower alkylene, lower heteroalkylene, —O-lower heteroalkylene, —S(O)ₙ-lower heteroalkylene, N(R_e)-lower heteroalkylene, —SO₂N(R_e)-lower heteroalkylene, lower heteroalkylene-SO₂N(R_e)—, —CON(R_e)-lower heteroalkylene, lower heteroalkylene-CON(R_e)—, —N(R_e)CON(R_f)-lower heteroalkylene, lower heteroalkylene-N(R_e)N(R_f)—, —N(R_e)SO₂N(R_f)-lower heteroalkylene, —N(R_e)—O-lower heteroalkylene, lower heteroalkylene-N(R_e)—O—, =N—O-lower alkylene, aryl and heteroaryl;

wherein Rₐ, Rᵦ, R_c, R_d, R_e and R_f are defined as above;

wherein when $L^1$ and $L^2$ may be linked together via a single bond, —O—, —S— or amide group to form a new 5 to 7 membered ring;

with the proviso that when A is an sp²-hybridized carbon atom and $X^2$ is rhodanine, $L^1$ is not —CH₂—CH₂—, —CH=CH—, —C≡C— or aryl.

In preferred embodiments, $X^2$ is selected from the group consisting of a 5 to 7 membered cycloalkyl ring, a 5 to 7 membered heterocycloalkyl ring containing from 1 to 3 heteroatoms, an aryl group and a heteroaryl group; A is selected from the group consisting of an sp²-hybridized carbon atom and an sp³-hybridized carbon atom; $L^2$ is a single bond; and $X^2$ and A are joined via a single or double bond.

In another preferred embodiment, the group —$X^2$—A— is selected from the group consisting of:

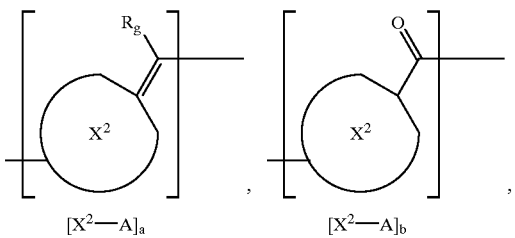

-continued

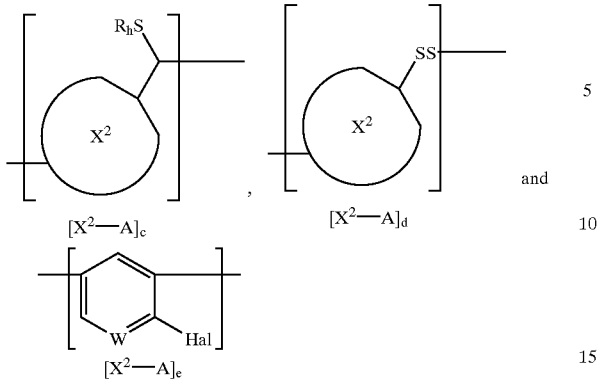

wherein $R_g$ is H, lower alkyl, lower alkoxy or F; $R_h$ is H, $-S(O)_n$-lower alkyl, $-S(O)_n$-lower heteroalkyl, $-S(O)_n$-aryl or $-S(O)_n$-heteroaryl; W is CH or N; Hal is a halogen atom; and $X^2$ is a substituted or unsubstituted member selected from 5–6 membered cycloalkyl, 5–6 membered heterocycloalkyl containing from 1 to 3 heteroatoms, heteroaryl containing from 1 to 3 heteroatoms and aryl.

In another group of embodiments, compounds are provided having the formula:

$$X^1-L^1-B-L^2-Ar^1 \qquad II$$

wherein

Ar$^1$ is substituted or unsubstituted aryl or substituted or unsubstituted heteroaryl;

$X^1$ is —H, substituted or unsubstituted alkyl, substituted or unsubstituted aryl, substituted or unsubstituted heteroaryl, —CN, —CO$_2$H, —SO$_3$H, —C(O)NHOH, —NH$_2$, —OH, —NH(lower alkyl), —O(lower alkyl), —N(lower alkyl)$_2$, or —C(O)—NH(3-tetrazolyl);

$L^1$ is a divalent linking group selected from —CH$_2$CH$_2$—, —CH=CH—, —C≡C—, —O—, —S(O)$_n$—, —N(R$_a$)—, —C(O)—, —C(O)O—, —SO$_2$N(R$_a$)—, —CON(R$_a$)—, —N(R$_a$)CON(R$_b$)—, —N(R$_a$)N(R$_b$)—, —N(R$_a$)SO$_2$N(R$_b$)—, —N(R$_a$)SO$_2$—, —N(R$_a$)—O—, =N—O—, lower alkylene, —O-lower alkylene, —S(O)$_n$-lower alkylene, N(R$_a$)-lower alkylene, —SO$_2$N(R$_a$)-lower alkylene, lower alkylene-SO$_2$N(R$_a$)—, —CON(R$_a$)-lower alkylene, lower alkylene-CON(R$_a$)—, —N(R$_a$)CON(R$_b$)-lower alkylene, lower alkylene-N(R$_a$)N(R$_b$)—, —N(R$_a$)SO$_2$N(R$_b$)-lower alkylene, —N(R$_a$)—O-lower alkylene, lower alkylene-N(R$_a$)—O—, =N—O-lower alkylene, lower heteroalkylene, —O-lower heteroalkylene, —S(O)$_n$-lower heteroalkylene, N(R$_a$)-lower heteroalkylene, —SO$_2$N(R$_a$)-lower heteroalkylene, lower heteroalkylene-SO$_2$N(R$_a$)—, —CON(R$_a$)-lower heteroalkylene, lower heteroalkylene-CON(R$_a$)—, —N(R$_a$)CON(R$_b$)-lower heteroalkylene, lower heteroalkylene-N(R$_a$)N(R$_b$)—, —N(R$_a$)SO$_2$N(R$_b$)-lower heteroalkylene, —N(R$_a$)—O-lower heteroalkylene, lower heteroalkylene-N(R$_a$)—O—, =N—O-lower alkylene, aryl and heteroaryl;

$L^2$ is a divalent linking group selected from —CH$_2$CH$_2$—, —(C(R$_c$)=C(R$_d$))$_m$—, —O—, —S(O)$_n$—, —N(R$_e$)—, —C(O)—, —C(O)O—, —SO$_2$N(R$_e$)—, —CON(R$_e$)—, —N(R$_c$)CON(R$_f$)—, —N(R$_e$)N(R$_f$)—, —N(R$_e$)SO$_2$N(R$_f$)—, —N(R$_e$)—O—, =N—O—, lower alkylene, perfluoro lower alkylene, polyfluoro lower alkylene, —O-lower alkylene, —S(O)$_n$-lower alkylene, N(R$_c$)-lower alkylene, —SO$_2$N(R$_e$)-lower alkylene, lower alkylene-SO$_2$N(R$_e$)—, —CON(R$_c$)-lower alkylene, lower alkylene-CON(R$_e$)—, —N(R$_e$)CON(R$_f$)-lower alkylene, lower alkylene-N(R$_e$)N(R$_f$)—, —N(R$_e$)SO$_2$N(R$_f$)-lower alkylene, —N(R$_e$)—O-lower alkylene, lower alkylene-N(R$_e$)—O—, =N—O-lower alkylene, lower heteroalkylene, —O-lower heteroalkylene, —S(O)$_n$-lower heteroalkylene, N(R$_e$)-lower heteroalkylene, —SO$_2$N(R$_e$)-lower heteroalkylene, lower heteroalkylene-SO$_2$N(R$_e$)—, —CON(R$_e$)-lower heteroalkylene, lower heteroalkylene-CON(R$_e$)—, —N(R$_e$)CON(R$_f$)-lower heteroalkylene, lower heteroalkylene-N(R$_e$)N(R$_f$)—, —N(R$_c$)SO$_2$N(R$_f$)-lower heteroalkylene, —N(R$_e$)—O-lower heteroalkylene, lower heteroalkylene-N(R$_e$)—O—, =N—O-lower alkylene, aryl and heteroaryl; wherein $R_a$, $R_b$, $R_c$, $R_d$, $R_e$ and $R_f$ are each independently selected from H, lower alkyl, lower heteroalkyl, —C(O)-lower alkyl, —C(O)-lower heteroalkyl, —S(O)$_2$-lower alkyl, and —S(O)$_2$-lower heteroalkyl; and the subscript n is an integer of from 0 to 2, the subscript m is an integer of from 0 to 3; and B is selected from:

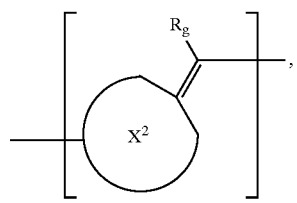

$B_a$

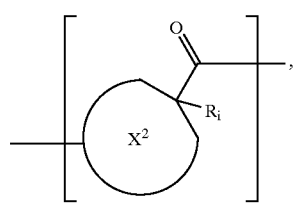

$B_b$

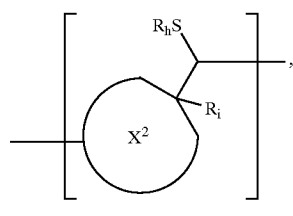

$B_c$

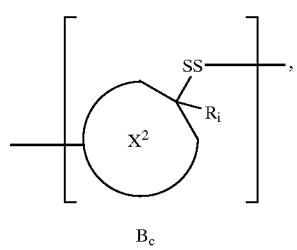

$B_c$

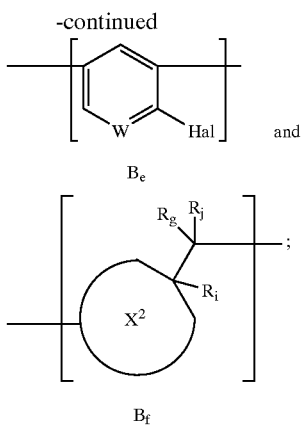

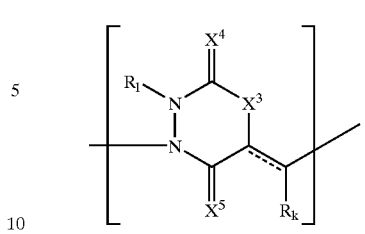

wherein $R_k$ is selected from H, lower alkyl, lower heteroalkyl and F; $R_l$ is H or lower alkyl; $X^3$ is O, S, $CH_2$, CH(lower alkyl), C(lower alkyl)$_2$, NH or N(lower alkyl); $X^4$ is selected from the group consisting of O, S, NH and N(lower alkyl), or $X^4$ and the carbon atom to which it is attached represents an sp$^3$-hybridized carbon having two substituents independently selected from H, lower alkyl and lower heteroalkyl; $X^5$ is selected from the group consisting of O, S, NH and N(lower alkyl), or $X^5$ and the carbon atom to which it is attached represents an sp$^3$-hybridized carbon having two substituents independently selected from the group consisting of H, lower alkyl, lower alkoxy, aryloxy, lower thioalkoxy and arylthioxy; and === represents either a single or double bond, with the proviso that when a single bond is intended, the ring atom bearing said single bond bears an additional substituent selected from the group consisting of H, lower alkyl, lower alkoxy and F. In other preferred embodiments, B is selected from:

wherein
- $X^2$ is a substituted or unsubstituted 5–6 membered cycloalkyl, 5–6 membered heterocycloalkyl containing from 1 to 3 heteroatoms, heteroaryl containing from 1 to 3 heteroatoms or aryl;
- W is CH or N;
- $R_g$ is H, lower alkyl, lower alkoxy or F;
- $R_h$ is H, —S(O)$_n$-lower alkyl, —S(O)$_n$-lower heteroalkyl, —S(O)$_n$-aryl or —S(O)$_n$-heteroaryl;
- $R_i$ is H, lower alkyl, lower heteroalkyl, or a bond that links the atom bearing $R_i$ with another atom in the $X^2$ ring;
- $R_j$ is H, lower alkyl, F or lower alkoxy; and
- Hal is a halogen atom;
- wherein when $L^1$ and $L^2$ may be linked together via a single bond, —O—, —S— or amide group to form a new 5 to 7 membered ring;

with the proviso that when B is

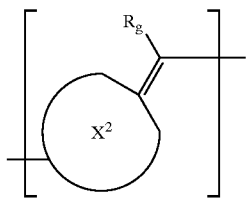

and $X^2$ is rhodanine, $L^1$ is not —CH$_2$—CH$_2$—, —CH=CH—, —C≡C— or aryl.

In preferred embodiments, B is selected from:

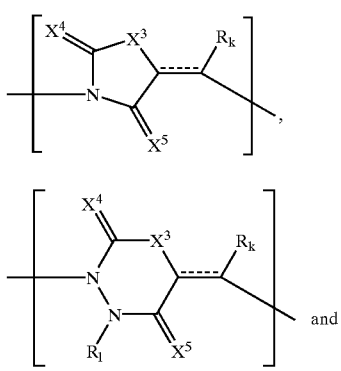

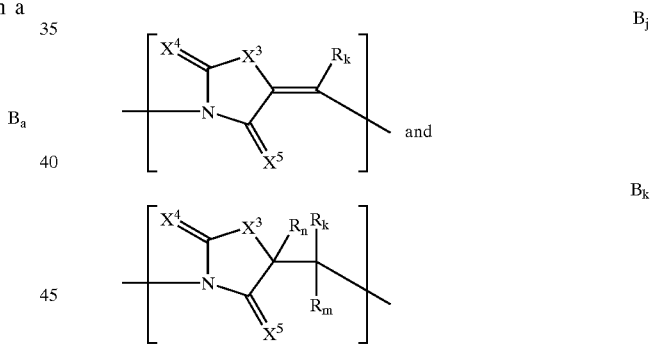

wherein $R_k$, $R_m$ and $R_n$ are each independently selected from the group consisting of H, F, lower alkyl and lower alkoxy; $X^3$ is selected from the group consisting of O, S, C(lower alkyl)$_2$, NH and N(lower alkyl); $X^4$ is selected from the group consisting of O and S, or $X^4$ and the carbon atom to which it is attached represents an sp$^3$-hybridized carbon having two substituents independently selected from the group consisting of H, lower alkyl and lower heteroalkyl; $X^5$ is selected from the group consisting of O and S, or $X^5$ and the carbon atom to which it is attached represents an sp$^3$-hybridized carbon having two substituents independently selected from the group consisting of H, lower alkoxy and lower thioalkoxy.

Still further preferred are those embodiments in which B is selected from:

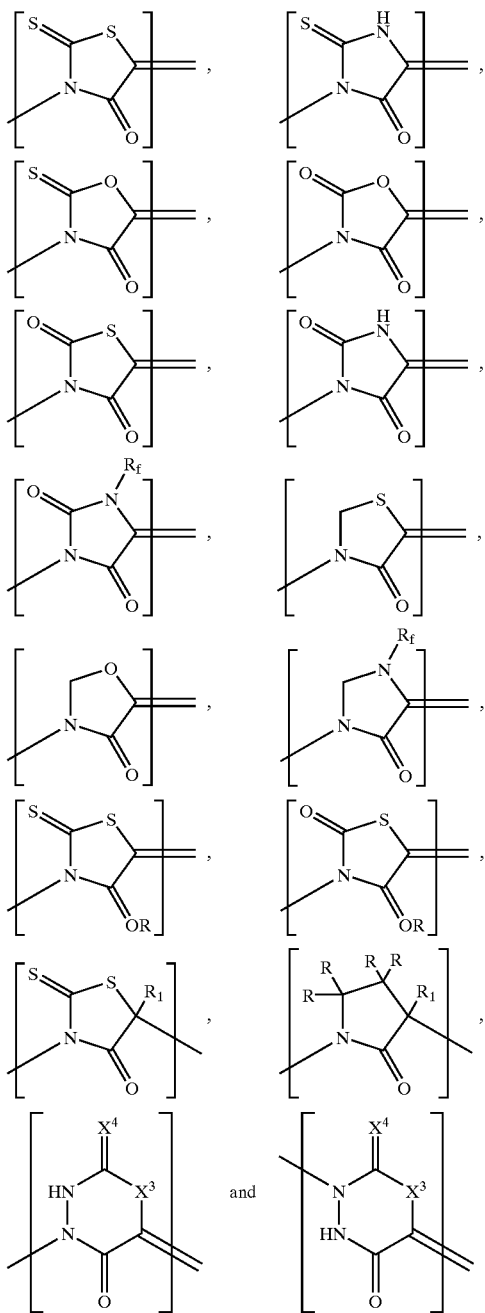

wherein $R_f$ and $R_l$ are defined as above and any unlabeled R groups are independently selected from H, lower alkyl, lower alkoxy and F.

Still other preferred embodiments are those in which B is selected from:

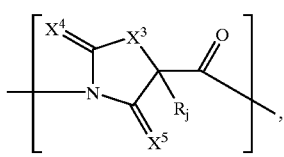

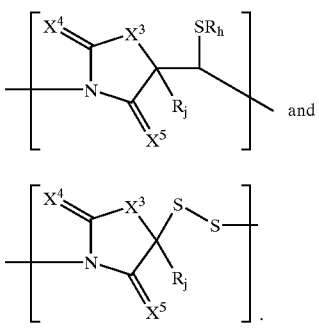

Returning to compounds of formula II, preferred embodiments are those in which $L^1$ is —N($R_a$)—, —N($R_a$)-alkylene, alkylene-SO$_2$—N($R_a$)—, —SO$_2$—N($R_a$)— or —N($R_a$)SO$_2$—; and $X^1$ is H, aryl or alkyl.

Also preferred are embodiments in which $Ar^1$ is selected from the group consisting of substituted or unsubstituted biphenyl group, substituted or unsubstituted bicyclic ring, substituted or unsubstituted phenyl group and substituted or unsubstituted pyridyl.

In the most preferred embodiments of the invention, the compound has the formula:

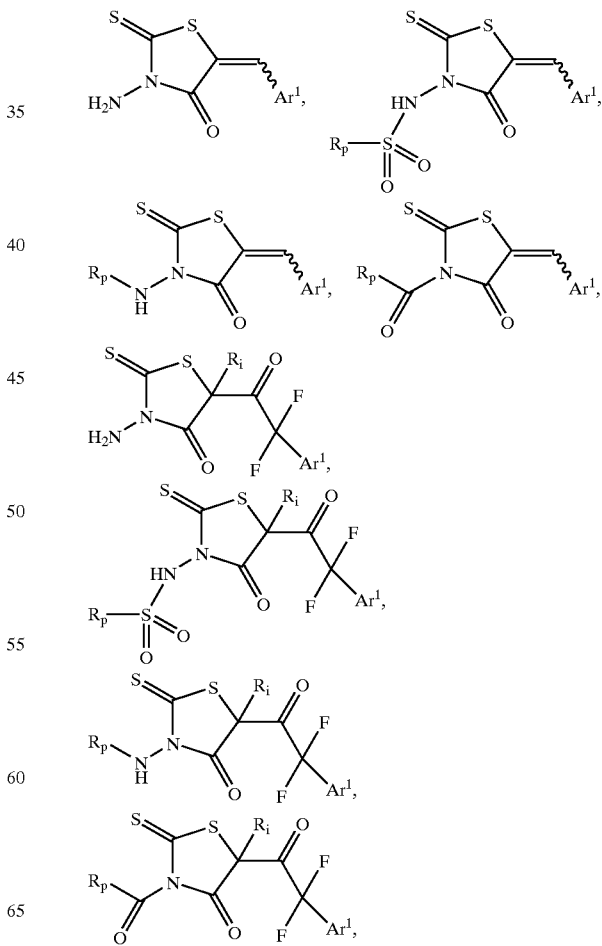

-continued

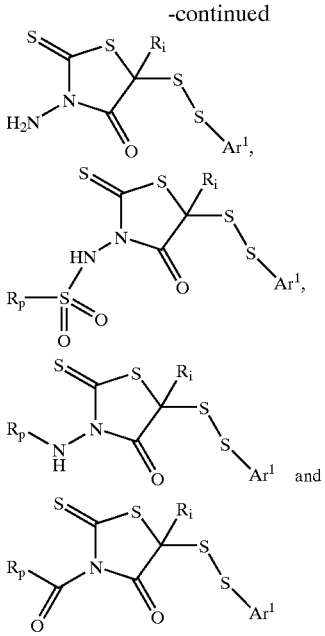

wherein R$_p$ is selected from the group consisting of substituted or unsubstituted alkyl, substituted or unsubstituted aryl and substituted or unsubstituted heteroaryl.

In another aspect, the invention provides compounds of the formula:

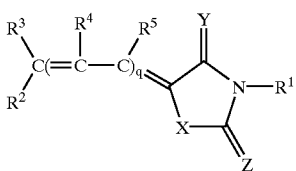

III wherein the subscript q is an integer of from 0 to 4; R$^1$ is hydrogen or a substituent having the formula L$^1$—COOH, wherein L$^1$ has the meaning provided above; X represents a moiety selected from —S—, —O—, and —N(R$_o$)—, wherein R$_o$ is H or lower alkyl; R$^2$ represents a substituted or unsubstituted aryl(C$_1$–C$_8$)alkyl, a substituted or unsubstituted aryl(C$_1$–C$_8$)alkenyl, a substituted or unsubstituted aryl(C$_1$–C$_8$)alkynyl, a substituted or unsubstituted alicyclic group having from 5–8 carbon atoms, or a group having the formula (R$_{2a}$)$_r$—(L)$_s$—R$_{2b}$—, wherein R$_{2a}$ and R$_{2b}$ can be the same or different and represent a substituted or unsubstituted heterocyclic group or a substituted or unsubstituted phenyl group and R$_{2a}$ can also represent a substituted or unsubstituted polycyclic group; R$^3$ represents H, substituted or unsubstituted (C$_1$–C$_8$)alkyl, substituted or unsubstituted aryl or substituted or unsubstituted heteroaryl and L represents a divalent linking group selected from methylene, ethylene, propylene, —CH═CH—, —C≡C—, —C(O)—, —O—, —S—, —S(O)—, —S(O)$_2$—, or —N(R$_{2c}$)— wherein R$_{2c}$ is selected from H or lower alkyl, and the subscripts r and s are each independently 0 or 1; Y represents O or S; Z represents O, S or N(R$_{2d}$) wherein R$_{2d}$ is H or lower alkyl or R$_{2d}$ and R$^1$ may be joined to form an imidazole or benzimidazole group, with the proviso that when R$^1$ is hydrogen, R$^3$ is not substituted furan.

More particularly, the invention provides compounds having the formula:

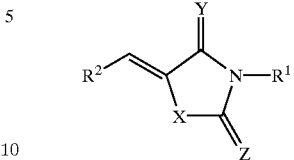

IV wherein R$^1$, R$^2$, X, Y and Z have the meanings provided above. More preferably, X is O, S or NH; Y is O or S; and Z is O, S or N(R$_{2d}$) wherein R$_{2d}$ is H or (C$_1$–C$_5$)alkyl or R$_{2d}$ is combined with R$^1$ to form a benzimidazole moiety.

Preferably, R$^2$ is a substituted or unsubstituted group selected from a heterocyclic group, a biphenyl group, a bicyclic ring, a phenyl group, and a cinnamenyl group. Preferred heterocyclic groups include furan, thiophene, oxadiazole, pyridine, pyrimidine, pyrazole, triazole, pyridazine, 1,3-oxathiolane, thiazole, thiadiazole, imidazole, pyrrole and triazine. Preferred bicyclic rings include benzofuran, isobenzofuran, benzothiophene, isobenzothiophene, benzoxazole, benzopyrrole, indolenine, 2-isobenzazole, benzpyrazole, quinoline, isoquinoline, 1,2-benzodiazine, 1,3-benzodiazine, 1,2,3-benzotriazole, benzothiazole, benzimidazole, 1,2,3-benzotriazine, and 1,2,4-benzotriazine.

In this group of embodiments, the heterocyclic and bicyclic ring substituents being selected from (C$_1$–C$_8$)alkyl, halogen, (C$_1$–C$_8$)alkoxy, hydroxy, nitro or a substituted or unsubstituted phenyl group; the phenyl group, biphenyl group and cinnamenyl group substituents being selected from carboxy, trifluoromethyl, (C$_1$–C$_8$)alkyl, halogen, (C$_1$–C$_8$)alkoxy, (C$_1$–C$_8$)acyloxy, cyano, carbalkoxy, (C$_1$–C$_8$)alkylthio, (C$_1$–C$_8$)alkylsulfinyl, (C$_1$–C$_8$)alkylsulfonyl, amino, (C$_1$–C$_8$)alkylamino, di(C$_1$–C$_8$)alkylamino, hydroxy, nitro, sulfonamido, or carboxamido.

In still another aspect, the invention provides compounds having the formula:

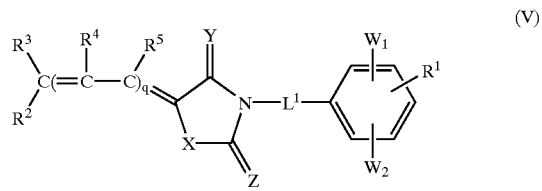

(V)

wherein R$^2$, R$^3$, R$^4$, R$^5$, q, X, Y, Z, and L$^1$ have the meanings provided above; R$^1$ is H, —OH, —COOR$_u$, —CONR$_v$R$_w$, —SO$_2$NR$_x$R$_y$ wherein R$_u$, R$_v$, R$_w$, R$_x$ and R$_y$ are H or lower alkyl, or R$^1$ is a mono-heterocyclic group selected from furan, thiophene, pyridine, pyrimidine, pyridazine, 1,3-oxathiolane, tetrazole, oxadiazole, oxazole, triazole, imidazoline, imidazole, thiazole, thiadiazole, pyrrole, piperidine, morpholine, triazine and pyrazole; and W$_1$ and W$_2$ are independently selected from H, (C$_1$–C8)alkyl, (C$_1$–C$_8$)alkenyl, (C$_1$–C$_8$)alkynyl, halogen, nitro, hydroxy, perfluoroalkyl, difluoromethyl, (C$_1$–C$_8$)alkoxy, phenoxy, phenyl(C$_1$–C$_8$)alkoxy, (C$_1$–C$_8$)acyl, (C$_1$–C$_8$)acyloxy, cyano, carbalkoxy, thio, (C$_1$–C$_8$)alkylthio, (C$_1$–C$_8$)alkylsulfunyl, (C$_1$–C$_8$)alkylsulfonyl, amino, (C$_1$–C$_8$)alkylamino, di(C$_1$–C$_8$)alkylamino, sulfonamido, carboxamido and (C$_1$–C$_8$)alkanoylamino.

In a preferred group of embodiments, the compound has the formula:

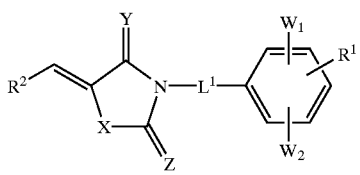

(VI)

wherein $R^1$, $L^1$, X, Y and Z have the meanings provided above. $W_1$ and $W_2$ are independently selected from H, $(C_1-C_8)$alkyl, $(C_1-C_8)$alkenyl, $(C_1-C_8)$alkynyl, halogen, nitro, hydroxy, perfluoroalkyl, difluoromethyl, $(C_1-C_8)$ alkoxy, phenoxy, $(C_1-C_8)$acyloxy, cyano, carbalkoxy, thio, $(C_1-C_8)$alkylthio, $(C_1-C_8)$alkylsulfinyl, $(C_1-C_8)$ alkylsulfonyl, amino, $(C_1-C_8)$alkylamino, di$(C_1-C_8)$ alkylamino, sulfonamido, carboxamido and $(C_1-C_8)$ alkanoylamino.

More preferably, X is O, S or $N(R_o)$, wherein $R_o$ is H or lower alkyl; Y is O or S; and Z is O, S or $N(R_{2d})$ wherein $R_{2d}$ is H or $(C_1-C_5)$alkyl.

$R^2$ is a substituted or unsubstituted mono- or bi-heterocyclic group, a substituted or unsubstituted polycyclic ring, a substituted or unsubstituted alicyclic group having 5–8 carbon atoms, a substituted or unsubstituted phenyl group, a substituted or unsubstituted biphenyl group, a substituted or unsubstituted phenylether group, a substituted or unsubstituted cinnamenyl group, or a substituted or unsubstituted stilbenyl group. Preferred mono-heterocyclic groups are selected from furan, thiophene, pyridine, pyrimidine, pyridazine, 1,3-oxathiolane, tetrazole, oxadiazole, oxazole, triazole, tetrazole, imidazoline, imidazole, thiazole, thiadiazole, pyrrole, piperidine, triazine and pyrazole. Preferred bi-heterocyclic groups are those having two mono-heterocyclic groups either linked together or fused (sharing two common ring vertices). Preferred polycyclic ring systems include benzofuran, isobenzofuran, benzothiophene, isobenzothiophene, benzoxazole, benzopyrrole, indolenine, 2-isobenzazole, benzpyrazole, quinoline, isoquinoline, 1,2-benzodiazine, 1,3-benzodiazine, 1,2,3-benzotriazole, benzothiazole, benzimidazole, 1,2,3-benzotriazine, 1,2,4-benzotriazine, naphthalene, anthracene, and fluorene.

Preferred substituents for the mono-heterocyclic groups, bi-heterocyclic groups, alicyclic groups, and polycyclic groups are $(C_1-C8)$alkyl, $(C_1-C_8)$alkenyl, $(C_1-C_8)$alkynyl, halogen, nitro, hydroxy, trifluoromethyl, $(C_1-C_8)$alkoxy, substituted or unsubstituted phenyl, substituted or unsubstituted phenyl$(C_1-C_8)$alkyl, substituted or unsubstituted phenyl$(C_1-C_8)$alkenyl, substituted or unsubstituted phenyl $(C_1-C_8)$alkynyl; carbalkoxy and thio.

Preferred substituents for the substituted phenyl group, substituted biphenyl group, substituted phenylether group, substituted cinnamenyl group, or substituted stilbenyl group include $(C_1-C_8)$alkyl, $(C_1-C_8)$alkenyl, $(C_1-C_8)$alkynyl, halogen, nitro, hydroxy, carboxy, trifluoromethyl, difluoromethyl, $(C_1-C_8)$alkoxy, phenoxy, $(C_1-C_8)$acyloxy, cyano, carbalkoxy, thio, $(C_1-C_8)$alkylthio, $(C_1-C_8)$ alkylsulfinyl, $(C_1-C_8)$alkylsulfonyl, amino, $(C_1-C_8)$ alkylamino, di$(C_1-C_8)$alkylamino, sulfonamido, carboxamido, $(C_1-C_8)$alkanoylamino, 1-pyrrolidyl, 1-piperidinyl or 4-morpholinyl.

Preferably, Y is O or S, and Z is O, S or $N(R_{2d})$ wherein $R_{2d}$ and $R^1$ are optionally linked to form an imidazole or benzimidazole ring.

In the most preferred embodiments, the compounds are selected from those having either of the formulae:

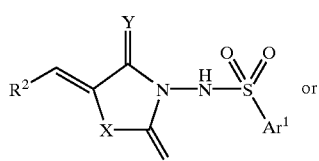

VIIa or

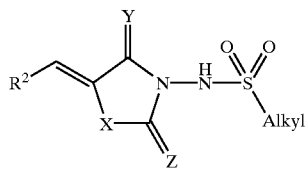

VIIb wherein X, Y and Z have the meanings provided for formula VI. Additionally, $Ar^1$ is selected from the group consisting of substituted or unsubstituted aryl and substituted or unsubstituted heteroaryl, and $R^2$ is a substituted or unsubstituted mono- or bi-heterocyclic group, a substituted or unsubstituted polycyclic ring, a substituted or unsubstituted alicyclic group having 5–8 carbon atoms, a substituted or unsubstituted phenyl group, a substituted or unsubstituted biphenyl group, a substituted or unsubstituted phenylether group, a substituted or unsubstituted cinnamenyl group, or a substituted or unsubstituted stilbenyl group. Preferred mono-heterocyclic groups are selected from furan, thiophene, pyridine, pyrimidine, pyridazine, 1,3-oxathiolane, tetrazole, oxadiazole, oxazole, triazole, tetrazole, imidazoline, imidazole, thiazole, thiadiazole, pyrrole, piperidine, triazine and pyrazole. Preferred bi-heterocyclic groups are those having two mono-heterocyclic groups either linked together or fused (sharing two common ring vertices). Preferred polycyclic ring systems include benzofuran, isobenzofuran, benzothiophene, isobenzothiophene, benzoxazole, benzopyrrole, indolenine, 2-isobenzazole, benzpyrazole, quinoline, isoquinoline, 1,2-benzodiazine, 1,3-benzodiazine, 1,2,3-benzotriazole, benzothiazole, benzimidazole, 1,2,3-benzotriazine, 1,2,4-benzotriazine, naphthalene, anthracene, and fluorene.

With regard to formulae VIIa and VIIb, the term alkyl is intended to include the full interpretation provided in the definitions above. Exemplary structures of compounds within this preferred group of embodiments are

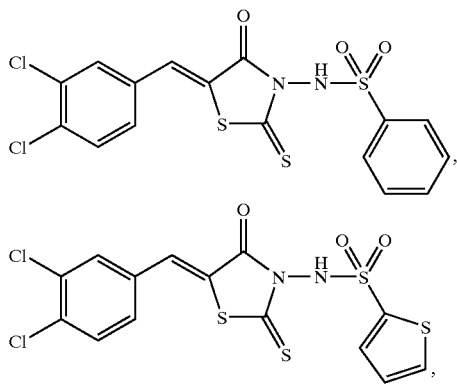

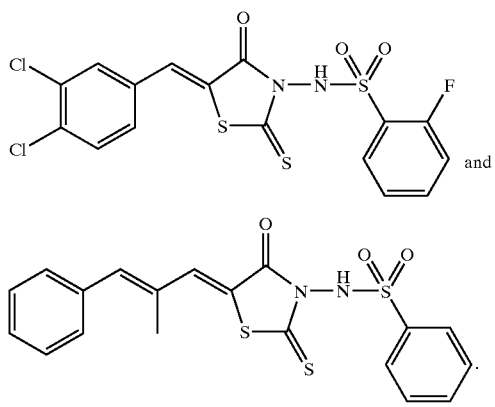

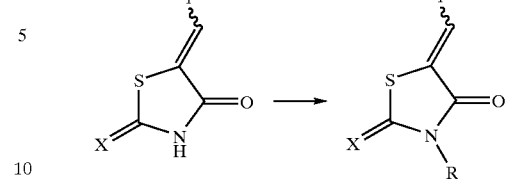

Scheme C

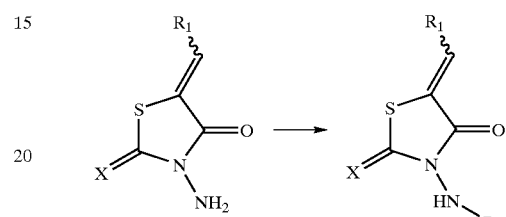

Scheme D

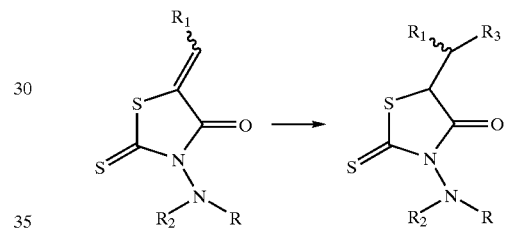

Scheme E

Preparation of the Compounds. Compounds of the present invention can be prepared as generally outlined in one or more of Schemes A–E below, and as provided in the examples. Of course, the compounds of the present invention can be prepared by any method known in the art, including the methods used to prepare the compounds that are commercially available.

Scheme A

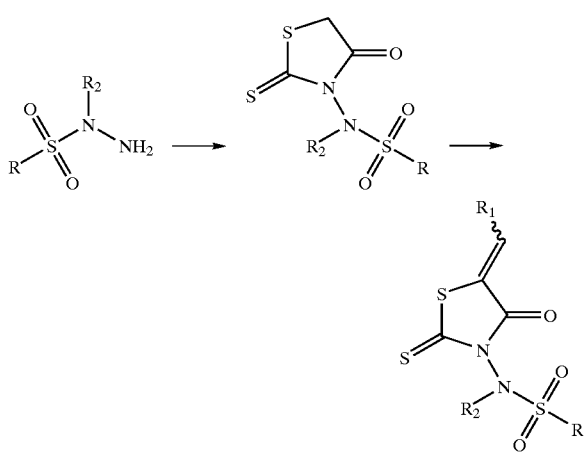

Scheme B

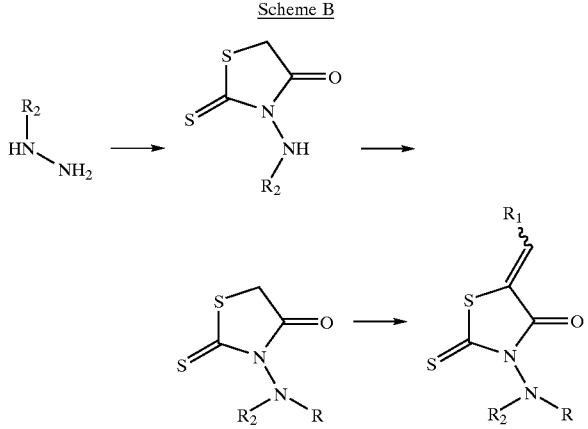

Scheme A illustrates the synthesis of N-substituted-3-(sulfonylamino)-5-(substitutedmethylene)rhodanine compounds. Sulfonylation of an appropriately substituted hydrazine may be followed by formation of the rhodanine ring upon treatment with bis(carboxymethyl)trithiocarbonate. Treatment of the resulting substituted rhodanine with base and an appropriate electrophile using methods known to those skilled in the art then results in the N-substituted 3-(sulfonylamino)-5-(sub stitutedmethylene)rhodanine.

Scheme B illustrates the synthesis of N-substituted and N-disubstituted 3-(sulfonylamino)-5-(substitutedmethylene)rhodanine compounds. Treatment of a substituted hydrazine with bis(carboxymethyl)trithiocarbonate followed by alkylation of the resulting substituted 3-aminorhodanine with an appropriate electrophile using methods known to those skilled in the art results in the substituted 3-aminorhodanine. Alkylation with a suitable electrophile such as an aldehyde then gives the N-substituted 3-amino-5-(substitutedmethylene)rhodanine compound.

Scheme C illustrates the alkylation, acylation or sulfonylation of a 5-substitutedmethylene-2-substituted-4-oxothiazolidine. Alkylation may be performed by treatment with an appropriate electrophile (for example, alkyl halide, acyl halide, sulfonyl halide) using methods known to those skilled in the art.

Scheme D illustrates alkylation or acylation of a 3-amino-5-substitutedmethylene-2-substituted-4-oxothiazolidine. Alkylation or acylation may be performed by treatment with an appropriate electrophile such as alkyl or acyl halide using methods known to those skilled in the art.

Scheme E illustrates addition to the double bond of a substituted 3-aminorhodanine. Addition may be performed by treatment with an appropriate nucleophile or hydride transfer agent using methods known to those skilled in the art.

Analysis of the Compounds. The subject compounds and compositions may be demonstrated to have pharmacological activity, e.g, antiviral activity, in in vitro and in vivo assays, as known in the art.

Certain preferred compounds and compositions are capable of specifically inhibiting or suppressing a viral infection, e.g., an HCV infection. An in vivo assessment of the antiviral activity of the compounds of the invention may be made using an animal model of viral infection, e.g., a primate model. Cell-based assays may be performed using, e.g, a cell line directly infected with a virus. Cell-based assays for activity against a specific viral component, e.g, a polymerase, may also be performed. Additionally, biochemical or mechanism-based assays, e.g., transcription assays using a purified protein, Northern blot, RT-PCR, etc., may be performed.

The above-described assays are exemplary and not intended to limit the scope of the invention. The skilled practitioner can appreciate that modifications can be made to conventional assays to develop equivalent assays that obtain the same result.

Combinatorial libraries of compounds that possess an electrophilic moiety capable of reacting with a thiol group can be screened for antiviral activity. Conventionally, new chemical entities with useful properties are generated by identifying a chemical compound (called a "lead compound") with some desirable property or activity, e.g., antiviral activity, creating variants of the lead compound, and evaluating the property and activity of those variant compounds. However, the current trend is to shorten the time scale for all aspects of drug discovery. Because of the ability to test large numbers of compounds quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et. al. (1994) *J. Med. Chem.* 37(9):1233–1251).

Preparation and screening of combinatorial chemical libraries is well known to those of skill in the art. Such combinatorial chemical libraries include, but are not limited to, peptide libraries (see, e.g., U.S. Pat. No. 5,010,175,Furka (1991) *Int. J. Pept. Prot. Res.* 37:487–493,Houghton et. al. (1991) *Nature* 354: 84–88), peptoid libraries (PCT Publication No WO 91/19735), encoded peptide libraries (PCT Publication WO 93/20242), random bio-oligomer libraries (PCT Publication WO 92/00091), benzodiazepine libraries (U.S. Pat. No. 5,288,514), libraries of diversomers, such as hydantoins, benzodiazepines and dipeptides (Hobbs et. al. (1993) *Proc. Nat. Acad. Sci. USA* 90:6909–6913), vinylogous polypeptide libraries (Hagihara et al. (1992) *J. Amer. Chem. Soc.* 114:6568), libraries of nonpeptidyl peptidomimetics with a Beta-D-Glucose scaffolding (Hirschmann et al. (1992) *J. Amer. Chem. Soc.* 114:9217–9218), analogous organic syntheses of small compound libraries (Chen et. al. (1994) *J. Am. Chem. Soc.* 116:2661), oligocarbamate libraries (Cho et al. (1993) *Science* 261:1303) and/or peptidyl phosphonate libraries (Campbell et al (1994) *J. Org. Chem.* 59:658). See, generally, Gordon et al. (1994) *J. Med. Chem.* 37:1385–1401, nucleic acid libraries (see, e.g., Stratagene Corp.), peptide nucleic acid libraries (see, e.g., U.S. Pat. No. 5,539,083), antibody libraries (see, e.g., Vaughn et. al (1996) *Nature Biotechnology* 14(3):309–314), and PCT/US96/10287), carbohydrate libraries (see, e.g., Liang et al. (1996) *Science* 274:1520–1522, and U.S. Pat. No. 5,593,853), and small organic molecule libraries (see, e.g., benzodiazepines, Baum (1993) *C&EN* January 18, page 33; isoprenoids, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky.; Symphony, Rainin, Woburn Mass.; 433A Applied Biosystems, Foster City Calif.; 9050 Plus, Millipore, Bedford, Mass.).

A number of well known robotic systems have also been developed for solution phase chemistries. These systems includes automated workstations like the automated synthesis apparatus developed by Takeda Chemical Industries, LTD. (Osaka, Japan) and many robotic systems utilizing robotic arms (Zymate II, Zymark Corporation, Hopkinton Mass.; Orca, Hewlett-Packard, Palo Alto Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see e.g., ComGenex, Princeton N.J.; AsInEx, Moscow, Russia; Tripos, Inc., St. Louis Mo.; ChemStar, Ltd, Moscow, Russia; 3D Pharmaceuticals, Exton Pa.; Martek Biosciences, Columbia Md.; etc.).

High throughput assays for the presence, absence, quantification, or other properties of particular compounds are well known to those of skill in the art. Such assays may be adapted to identify compounds capable of modifying a viral RNA-dependent RNA polymerase protein, e.g., NS5B, using functional protein. Preferred assays thus detect enhancement or inhibition of HCV RNA-dependent RNA polymerase activity.

In addition, high throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Compositions

In view of the antiviral activity associated with the compounds described above, the present invention further provides pharmaceutical compositions comprising one or more of the above compounds in combination with a pharmaceutically acceptable excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Still other compositions of the present invention are those that combine two or more of the present compounds in one formulation, or one compound from the present invention with a second antiviral agent. Suitable antiviral agents include, in general acyclovir, famciclovir, ganciclovir, foscarnet, idoxuridine, sorivudine, trifluridine, valacyclovir, cidofovir, didanosine, stavudine, zalcitabine, zidovudine, ribavirin, amantadine, rimantidine and oseltamivir.

Methods of Use

In yet another aspect, the present invention provides novel methods for the use of the foregoing compounds and compositions. In particular, the invention provides novel methods for treating or preventing viral infections, e.g., HCV infection. The invention also provides novel methods for treating or preventing diseases resulting from, in whole or in part, viral infections, preferably diseases resulting from, in whole or in part, HCV infection, such as hepatitis C, cirrhosis, chronic liver disease and hepatocellular carcinoma. The methods typically involve administering to a patient an effective amount of one or more of the subject compounds or compositions.

The compositions may be advantageously combined and/ or used in combination with other antiviral agents which are either therapeutic or prophylactic agents, and different from the subject compounds. The compositions may also be advantageously combined and/or used in combination with agents that treat conditions often associated with the viral infections that are sensitive to the present compounds, such as anti-HIV agents or immunosuppressive agents. In many instances, administration in conjunction with the subject compositions enhances the efficacy of such agents. Accordingly, the present compounds, when combined or administered in combination with other antiviral agents, can be used in dosages which are less than the expected amounts when used alone, or less than the calculated amounts for combination therapy.

Exemplary treatment options for hepatitis C (HCV) include interferons, e.g., interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors (e.g., ViroPharma's VP50406 series), antisense agents, therapeutic vaccines, protease inhibitors, helicase inhibitors and antibody therapy (monoclonal and polyclonal).

The compounds and compositions of the present invention may also be used with agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

EXAMPLES

Reagents and solvents used below can be obtained from commercial sources such as Aldrich Chemical Co. (Milwaukee, Wis. USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Examples 1–8 illustrate suitable methods of synthesis of representative compounds described in this invention.

Example 1

5-(4-chlorophenylmethylene)-3-amino-4-oxo-2-thionothiazolidine (1).

A flask containing 15 mL methanol was charged with 1.0 g rhodanine (7.51 mmol, 1.0 equiv), 2.11 g 4-chlorobenzaldehyde (15.02 mmol, 2.0 equiv), and 1.85 g NaOAc (22.5 mmol, 3.0 equiv). The solution was allowed to stir at 65° C. for 2.2 h. The resulting slurry was removed from the bath, and the yellow solid was filtered off. The solid was washed (5×MeOH) and dried under vacuum to give 638 mg of product (2.50 mmol, 33%). $^1$H NMR (DMSO, 400 MHz) δ 7.87 (s, 1 H), 7.70 (d, J=8.61 Hz, 2 H), 7.64 (d, J=8.7 Hz, 2 H), 5.95 (s, 2 H). Anal. calcd for $C_{10}H_7ClN_2OS_2$: C, 44.36; H, 2.61; N, 10.35; S, 23.69. Found: C, 44.43; H, 2.61; N, 10.34; S, 23.54.

Example 2

5-(4-fluorophenylmethylene)-3-(benzenesulfonylamino)-4-oxo-2-thionothiazolidine (2). 3-(Benzenesulfonylamino)-4-oxo-2-thionothiazolidine: Benzenesulfonyl hydrazide (25 g, 145 mmol) was suspended in 300 mL water and heated to 95° C. After 2 hours the hydrazide was fully dissolved and 32.85 g bis(carboxymethyl)trithiocarbonate (145 mmol, 1.0 equiv) was added. The resulting solution was stirred for 20 h, and was then removed from the heat bath. The resulting yellow solid was filtered, and washed (3×$H_2O$). The solid was then recrystallized from hot EtOH to give the product as light yellow crystals 16.39 g (56.91 mmol, 39%).

5-(4-fluorophenylmethylene)-3-(benzenesulfonylamino)-4-oxo-2-thionothiazolidine: 3-(Benzenesulfonylamino)-4-oxo-2-thionothiazolidine 624 mg (2.17 mmol, 1.0 equiv) was combined with 349 μL 4-fluorobenzaldehyde (3.26 mmol, 1.5 equiv) and 18 mg NaOAc (0.217 mmol, 0.1 equiv) in 8 mL MeOH. The solution was allowed to stir for 5 h, at which time the resulting yellow solid was removed via filtration. The solid was washed (4×MeOH) and dried under vacuum to give the product as a yellow solid 83.5 mg (0.212 mmol, 10%). $^1$H NMR (DMSO, 400 MHz) δ 7.90–9.86 (m, 3 H), 7.77–7.70 (m, 3 H), 7.61 (t, J=8.8 Hz, 2 H), 7.42 (t, J=8.8 Hz, 2 H).

Example 3

5-(3,4-dichlorophenylmethylene)-3-(methanesulfonylamino)-4-oxo-2-thionothiazolidine (3).

3-(Methanesulfonylamino)-4-oxo-2-thionothiazolidine: Methanesulfonyl hydrazide (12.2 g, 110 mmol) was dissolved in 100 mL $H_2O$ and the solution was heated to 95° C. followed by the addition of 25 g bis(carboxymethyl)trithiocarbonate (110 mmol, 1.0 equiv). The solution was allowed to stir at 95° C. for 16 h, and then the bath was removed and the solution was allowed to cool to rt. The solution was extracted (3×$CH_2Cl_2$) and the organic portion was washed 1×$H_2O$. The combined organics were dried ($Na_2SO_4$) and concentrated under reduced pressure. Purification by flash chromatography ($SiO_2$, 2% MeOH:$CH_2Cl_2$) gave the product as a tacky yellow resin 14.13 g (62.54 mmol, 57%).

5-(3,4-dichlorophenylmethylene)-3-(methanesulfonylamino)-4-oxo-2-thionothiazolidine: 3-(Methanesulfonylamino)-4-oxo-2-thionothiazolidine 269 mg (1.19 mmol, 1.0 equiv) was dissolved in 3 mL MeOH followed by the addition of 208 mg 3,4-dichlorobenzaldehyde (1.19 mmol, 1.0 equiv) and 10 mg NaOAc (0.119 mmol, 0.1 equiv). The solution was allowed to stir for 24 hours, at which time the yellow solid was removed by filtration. The solid was washed (4×MeOH) and dried under vacuum to give the 248 mg of the product as a yellow solid (0.649 mmol, 55%). $^1$H NMR (DMSO, 400 MHz) δ 8.01 (d, J=1.0 Hz, 1 H), 7.95 (s, 1 H), 7.84 (d, J=8.4 Hz, 1 H), 7.63 (dd, J=2.1, 8.4 Hz, 1 H), 3.28 (s, 3 H).

Example 4

5-(3,4-dichlorophenylmethylene)-3-(benzoyl)-4-oxo-2-thionothiazolidine (4). A 50 mL flask was charged with 899 mg rhodanine (6.75 mmol, 1.0 equiv), 1.77 g 3,4-dichlorobenzaldehyde (10.1 mmol, 1.5 equiv), 1.66 g sodium acetate (20.25 mmol, 3.0 equiv) and 20 mL methanol. The mixture was heated to 65° C. with stirring for 1.75 h. The yellow solid was then filtered and washed (4×MeOH) to give the product 5-(3,4-dichlorophenylmethylene)-4-oxo-2-thionothiazolidine as a yellow solid (1.059 g 3.67 mmol, 54%).

5-(3,4-dichlorophenylmethylene)-4-oxo-2-thionothiazolidine (100 mg, 0.345 mmol, 1.0equiv) was suspended in 653 μL of anhydrous pyridine, followed by the addition of 44 μL benzoyl chloride (0.379 mmol, 1.1 equiv). After about 2 minutes a yellow precipitate formed. The reaction was stirred at rt for 30 minutes. The pyridine was evaporated and the residue was purified by column chromatography ($SiO_2$, EtOAc/hexanes) to yield 62 mg of 5-(3,4-dichlorophenylmethylene)-3-(benzoyl)-4-oxo-2-thionothiazolidine (0.157 mmol, 46%) as a yellow solid. Anal. calcd for $C_{17}H_9Cl_2NO_2S_2$: C, 51.78; H, 2.30; N, 3.55; S, 16.26. Found: C, 52.04; H, 2.47; N, 3.48; S, 16.26.

Example 5

5-(3,4-dichlorophenylmethylene)-2,4-thiazolidinedione (5). A flask was charged with 5-(3,4-dichlorophenylmethylene)-4-oxo-2-thionothiazolidine (prepared as in example 4 above, 250 mg, 0.868 mmol, 1.0 equiv) followed by the addition of 1.7 mL pyridine and 3-chlorobenzenesulfonyl chloride (215 mg, 1.018 mmol, 1.2 equiv). The flask was sealed and placed in a 95° C. oil bath for 2.5 hrs. Following heating ice water was added to the reaction mixture, and the dark brown precipitate was collected by filtration. The precipitate was washed (3×$H_2O$) then dissolved in methylene chloride. The methylene chloride solution was dried with sodium sulfate, filtered, and concentrated under reduced pressure. The residue obtained was purified by column chromatography ($SiO_2$, EtOAc/hexanes) to yield 34.6 mg (0.126 mmol, 14%) of the product 5-(3,4-dichlorophenylmethylene)-2,4-thiazolidinedione as a beige solid. Anal. calcd for $C_{10}H_5Cl_2NO_2S$: C, 43.81; H, 1.84; Cl, 25.87; N, 5.11; S, 11.70. Found: C, 43.83; H, 185; N, 5.10; Cl, 25.76; S,11.71.

Example 6

5-(3,4-dichlorophenylmethylene)-3-(4-chlorobenzenesulfonyl)-4-oxo-2-thionothiazolidine (6). A flask was charged with 5-(3,4-dichlorophenylmethylene)-4-oxo-2-thionothiazolidine (prepared as in example 4 above, 300 mg, 1.038 mmol, 1.0 equiv), 4-chlorobenzene sulfonyl chloride (329 mg, 1.557 mmol, 1.5 equiv), and 2 mL of DMF. Sodium hydride (60% in mineral oil, 63 mg, 1.557 mmol, 1.5 equiv) was then added in one portion. The reaction was stirred at rt overnight. After 24 h, water was added to the reaction, and the mixture was then extracted with methylene chloride. The methylene chloride solution was dried with sodium sulfate, filtered and concentrated under reduced pressure. Crystallization from methylene chloride yielded 3 mg (6.4 μmol, 0.6%) of product 5-(3,4-dichlorophenylmethylene)-3-(4-chlorobenzenesulfonyl)-4-oxo-2-thionothiazolidine as a yellow solid. FAB-MS: m/z 486 (M+Na$^+$).

Example 7

3-(3,4-dichlorophenylmethylene)-1-(4-fluorobenzenesulfonyl)-5-methyl-2-pyrrolidinone (7). A flame dried flask was charged with 444 mg sodium hydride (60% wt in oil, 11.1 mmol, 1.1 equiv) under N$_2$. The solid was washed (2×hexanes) followed by the addition of 100 mL anhydrous THF. The solution was cooled to 0° C. followed by the addition of 1 g 5-methyl-2-pyrrolidinone (10.09 mmol, 1.0 equiv). The solution was allowed to stir for 20 min, followed by the addition of 1.96 g 4-fluorobenzenesulfonyl chloride (10.09 mmol, 1.0 equiv) in 10 mL THF. After stirring for an additional 50 min, the solution was diluted with sat. NaHCO$_3$, and the THF was removed under reduced pressure. The solution was then extracted (3×EtOAc), dried (MgSO$_4$), and concentrated under reduced pressure. Purification by flash chromatography (SiO$_2$, 30% EtOAc/hexanes) gave the product 1-(4-fluorobenzenesulfonyl)-5-methyl-2-pyrrolidinone as a white solid (949 mg, 3.69 mmol, 37%).

A flame dried flask was charged with 332 mg 1-(4-fluorobenzenesulfonyl)-5-methyl-2-pyrrolidinone (prepared above, 1.29 mmol, 1.0 equiv) and 10 mL THF under N$_2$. The solution was cooled to −78° C. followed by the addition of 1.68 mL of a 1.0 M solution of sodium bis(trimethylsilyl) amide (1.68 mmol, 1.3 equiv). The solution was allowed to stir for an additional 40 min followed by the addition of 271 mg 3,4-dichlorobenzaldehyde (1.54 mmol, 1.2 equiv) in 2 mL THF. After stirring an additional 10 min, the solution was diluted with 10 mL 0.1 N HCl and allowed to warm to rt. The solution was then extracted (3×Et$_2$O), washed with brine, dried (MgSO$_4$), and concentrated under reduced pressure. Purification via flash chromatography (SiO$_2$, 1% MeOH/CH$_2$Cl$_2$) gave the product 3-(3,4-dichlorophenylmethylene)-1-(4-fluorobenzenesulfonyl)-5-methyl-2-pyrrolidinone as a white foam (39 mg, 0.0937 mmol, 7%). $^1$H NMR (DMSO, 400 MHz) δ 8.28 (m, 2 H), 7.96 (d, J=2 Hz, 1H), 7.85 (d, J=8.4 Hz, 1 H), 7.70–7.63 (m, 3 H), 7.45 (t, J=2.9 Hz, 1 H), 4.86 (m, 1 H), 3.59 (m, 1 H), 2.92 (m, 1 H), 1.56 (d, J=6.0 Hz, 3 H).

Example 8

5-(3,4-dichlorophenyl-1-ethylene)-3-(benzenesulfonylamino)-4-oxo-2-thionothiazolidine (8). A 50 mL flask equipped with a Dean-Stark trap and condenser was charged with 486 mg 3-(benzenesulfonylamino)-4-oxo-2-thionothiazolidine (prepared as in example 2, 1.688 mmol, 1.0 equiv), 319 mg 3,4-dichloroacetophenone (1.688 mmol, 1.0 equiv), 1.84 mL piperidine (13.07 mmol, 11.0 equiv), 3.84 mL acetic acid (67.5 mmol, 40.0 equiv), and 25 mL benzene. The solution was heated to reflux for 6 h, followed by removal of the volatile components under reduced pressure. Purification via flash chromatography (SiO$_2$, 2% MeOH/hexanes) gave the product as a yellow solid (22 mg, 0.0483 mmol, 3%). $^1$H NMR (DMSO, 400 MHz, mixture of olefin isomers) δ (major isomer) 7.83 (m, 2 H), 7.80 (m, 1 H), 7.69 (m, 1 H), 7.65–7.55 (m, 3 H), 7.51 (m, 1H), 2.7 (s, 3 H); ESI-MS m/z 458.1 (M+H$^+$).

Example 9

Compounds of the present invention were evaluated for HCV NS5B inhibitory activity. IC$_{50}$ values, representing the concentration of the compound at which 50% of the activity is inhibited, were measured as described below. A substantial number of the compounds exhibited IC$_{50}$ values ranging from less than 1 to about 30 μM or more.

Materials

Figure 3:
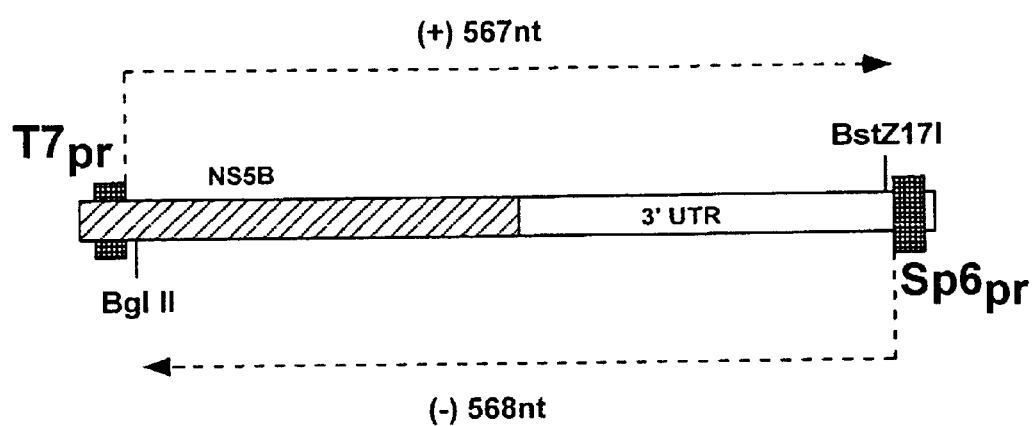
FIG. 3 provides the structure of an HCV 3'-UTR RNA template used to evaluate compounds for HCV polymerase inhibitory activity.

Recombinant HCV Δ21 NS5B polymerase purified from *E. coli*
Template: Transcribed HCV 3' UTR RNA (567 nt) (FIG. 3)
Signal Detection: $^{32}$P or $^{33}$P CTP incorporation

| Methods | |
|---|---|
| Template/Label Mixture (per reaction) | Enzyme Dilution Mixture (per reaction) |
| 5 mM MgCl$_2$ | 20 mM Tris 7.5 |
| 2 mM DTT | 30 mM KCl |
| 5 μM ATP | 2 mM DTT |
| 1 μM UTP | 10% Glycerol |
| 0.05 μM CTP | 100 nM HCV Δ21 NS5B polymerase |
| 0.05 μM 3' UTR RNA Template | H$_2$O to 10 μL |
| 0.001 to 0.1 μCi $^{32}$P CTP | |
| H$_2$O to 40 μL | |

1. Assay was initiated by mixing 40 μL of template/label mixture with 10 μL of enzyme dilution mixture.
2. The assay plates were covered and incubated at 41° C. for 60 min.
3. Reactions were filtered through 96-well DEAE-81 filter plates via vacuum to capture labeled reaction products. Plates were then washed under vacuum with multiple volumes of 0.5 M NaHPO$_4$ or 2×PBS to remove unincorporated label. The plates were counted to assess the level of product synthesis over background controls.

Protocol

1. Compounds were serially diluted as 20×stock in DMSO in 96-well plate, usually from 2 to 600 μM. Controls were enzyme without compound (100% activity remaining) and no enzyme (0% activity background).
2. Template label mixture was added first to assay plates. 2.5 μL of each compound dilution was added by multichannel pipetting to each mixture, according to predetermined pattern. Enzyme/no enzyme mix was added next according to pattern and mixed. Assay plates were incubated and processed as above. A large scale semiroboticized version was devised from this format to screen large numbers of individual compounds employing a customized assay plate that could be used to incubate the reaction and capture the incorporated products simultaneously.
3. Data were analyzed using commercially available software, e.g., Excel (Microsoft).

FIG. 2 provides structures and activity for several examples of compounds of the present invention. Activity is listed as follows: IC$_{50}$≦30 μM, ++; IC$_{50}$>30 μM, +.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula (VIIa):

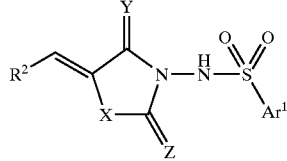

wherein
Ar¹ is selected from the group consisting of substituted or unsubstituted aryl and substituted or unsubstituted heteroaryl;
X is selected from —S—, —O— and —N(R$_O$)—, wherein R$_O$ is H or lower alkyl;
Y is O or S; and
Z is O, S or N(R$_{2d}$), wherein R$_{2d}$ is H or lower alkyl, or R$_{2d}$ and R¹ may be joined to form an imidazole or benzimidazole group; and
R² is a substituted or unsubstituted mono- or bi-heterocyclic group, a substituted or unsubstituted polycyclic ring, a substituted or unsubstituted alicyclic group having 5–8 carbon atoms, a substituted or unsubstituted phenyl group, a substituted or unsubstituted biphenyl group, a substituted or unsubstituted phenylether group, a substituted or unsubstituted cinnamenyl group, or a substituted or unsubstituted stilbenyl group.

2. The compound of claim 1 wherein said compound is selected from the group consisting of

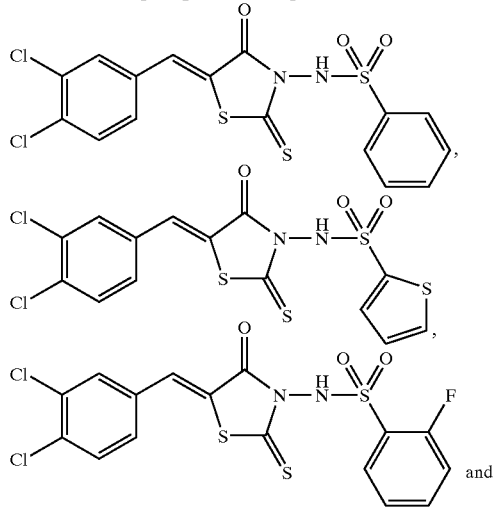

-continued

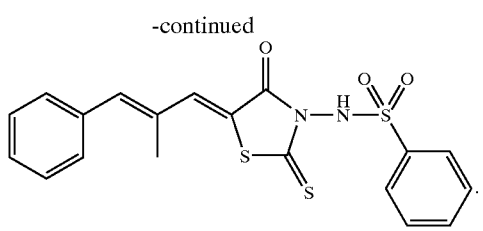

3. A pharmaceutical composition, comprising a pharmaceutically acceptable carrier and a therapeutically or prophylactically effective amount of a compound of claim 1.

4. A method for the treatment or prevention of a viral infection, comprising
administering to a subject suffering from or at risk for said viral infection an effective amount of a compound of claim 1.

* * * * *

UNITED STATES PATENT AND TRADEMARK OFFICE
CERTIFICATE OF CORRECTION

PATENT NO. : 6,727,267 B2
DATED : April 27, 2004
INVENTOR(S) : Jaen et al.

Page 1 of 1

It is certified that error appears in the above-identified patent and that said Letters Patent is hereby corrected as shown below:

Column 35,
Between lines approximately 4 and 7, delete the vertical line following the first hexagonal component in the chemical drawing, as shown below.
" "

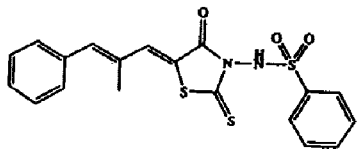

should be replaced with

-- 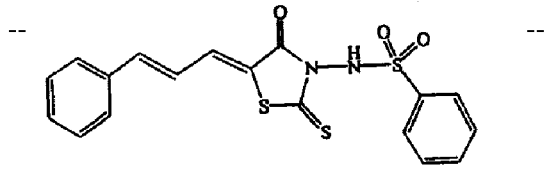 --

Signed and Sealed this

Seventh Day of June, 2005

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 591
<212> TYPE: PRT
<213> ORGANISM: Hepatitis C virus
<220> FEATURE:
<223> OTHER INFORMATION: HCV NS5B RNA-dependent RNA polymerase (RdRp)
      (EC 2.7.7.48)

<400> SEQUENCE: 1

Ser Met Ser Tyr Thr Trp Thr Gly Ala Leu Ile Thr Pro Cys Ala Ala
1               5                   10                  15

Glu Glu Ser Lys Leu Pro Ile Asn Pro Leu Ser Asn Ser Leu Leu Arg
            20                  25                  30

His His Ser Met Val Tyr Ser Thr Thr Ser Arg Ser Ala Ser Leu Arg
        35                  40                  45

Gln Lys Lys Val Thr Phe Asp Arg Leu Gln Val Leu Asp Asp His Tyr
    50                  55                  60

Arg Asp Val Leu Lys Glu Met Lys Ala Lys Ala Ser Thr Val Lys Ala
65                  70                  75                  80

Arg Leu Leu Ser Ile Glu Glu Ala Cys Lys Leu Thr Pro Pro His Ser
                85                  90                  95

Ala Lys Ser Lys Phe Gly Tyr Gly Ala Lys Asp Val Arg Ser Leu Ser
            100                 105                 110

Ser Arg Ala Val Asn His Ile Arg Ser Val Trp Glu Asp Leu Leu Glu
        115                 120                 125

Asp Thr Glu Thr Pro Ile Asp Thr Thr Ile Met Ala Lys Asn Glu Val
    130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Thr Leu Pro Gln Ala Val Met Gly Pro Ser Tyr Gly
            180                 185                 190

Phe Gln Tyr Ser Pro Gly Gln Arg Val Glu Phe Leu Val Asn Thr Trp
        195                 200                 205

Lys Ser Lys Lys Cys Pro Met Gly Phe Ser Tyr Asp Thr Arg Cys Phe
    210                 215                 220

Asp Ser Thr Val Thr Glu Asn Asp Ile Arg Thr Glu Glu Ser Ile Tyr
225                 230                 235                 240

Gln Cys Cys Asp Leu Ala Pro Glu Ala Arg Gln Ala Ile Arg Ser Leu
                245                 250                 255

Thr Glu Arg Leu Tyr Val Gly Gly Pro Leu Thr Asn Ser Lys Gly Gln
            260                 265                 270

Asn Cys Gly Tyr Arg Arg Cys Arg Ala Ser Gly Val Leu Thr Thr Ser
        275                 280                 285

Cys Gly Asn Thr Leu Thr Cys Tyr Leu Lys Ala Thr Ala Ala Cys Arg
    290                 295                 300

Ala Ala Lys Leu Gln Asp Cys Thr Met Leu Val Asn Gly Asp Asp Leu
305                 310                 315                 320

Val Val Ile Cys Glu Ser Ala Gly Thr Gln Glu Asp Ala Ala Ala Leu
                325                 330                 335

Arg Ala Phe Thr Glu Ala Met Thr Arg Tyr Ser Ala Pro Pro Gly Asp
```

-continued

| | | | | 340 | | | | | 345 | | | | | 350 | |
|---|---|---|---|---|---|---|---|---|---|---|---|---|---|---|---|
| Pro | Pro | Gln | Pro | Glu | Tyr | Asp | Leu | Glu | Leu | Ile | Thr | Ser | Cys | Ser | Ser |
| | | 355 | | | | | 360 | | | | | 365 | | | |
| Asn | Val | Ser | Val | Ala | His | Asp | Ala | Ser | Gly | Lys | Arg | Val | Tyr | Tyr | Leu |
| | | 370 | | | | | 375 | | | | | 380 | | | |
| Thr | Arg | Asp | Pro | Thr | Thr | Pro | Leu | Ala | Arg | Ala | Ala | Trp | Glu | Thr | Val |
| 385 | | | | | 390 | | | | | 395 | | | | | 400 |
| Arg | His | Thr | Pro | Val | Asn | Ser | Trp | Leu | Gly | Asn | Ile | Ile | Met | Tyr | Ala |
| | | | 405 | | | | | 410 | | | | | 415 | | |
| Pro | Thr | Leu | Trp | Ala | Arg | Met | Ile | Leu | Met | Thr | His | Phe | Phe | Ser | Ile |
| | | | 420 | | | | | 425 | | | | | 430 | | |
| Leu | Leu | Ala | Gln | Glu | Gln | Leu | Glu | Lys | Ala | Leu | Asp | Cys | Gln | Ile | Tyr |
| | | | 435 | | | | | 440 | | | | | 445 | | |
| Gly | Ala | Cys | Tyr | Ser | Ile | Glu | Pro | Leu | Asp | Leu | Pro | Gln | Ile | Ile | Glu |
| | | 450 | | | | | 455 | | | | | 460 | | | |
| Arg | Leu | His | Gly | Leu | Ser | Ala | Phe | Ser | Leu | His | Ser | Tyr | Ser | Pro | Gly |
| 465 | | | | | 470 | | | | | 475 | | | | | 480 |
| Glu | Ile | Asn | Arg | Val | Ala | Ser | Cys | Leu | Arg | Lys | Leu | Gly | Val | Pro | Pro |
| | | | | 485 | | | | | 490 | | | | | 495 | |
| Leu | Arg | Val | Trp | Arg | His | Arg | Ala | Arg | Ser | Val | Arg | Ala | Lys | Leu | Leu |
| | | | 500 | | | | | 505 | | | | | 510 | | |
| Ser | Gln | Gly | Gly | Arg | Ala | Ala | Thr | Cys | Gly | Lys | Tyr | Leu | Phe | Asn | Trp |
| | | | 515 | | | | | 520 | | | | | 525 | | |
| Ala | Val | Lys | Thr | Lys | Leu | Lys | Leu | Thr | Pro | Ile | Pro | Ala | Ala | Ser | Gln |
| | | 530 | | | | | 535 | | | | | 540 | | | |
| Leu | Asp | Leu | Ser | Gly | Trp | Phe | Val | Ala | Gly | Tyr | Asn | Gly | Gly | Asp | Ile |
| 545 | | | | | 550 | | | | | 555 | | | | | 560 |
| Tyr | His | Ser | Leu | Ser | Arg | Ala | Arg | Pro | Arg | Trp | Phe | Met | Leu | Cys | Leu |
| | | | | 565 | | | | | 570 | | | | | 575 | |
| Leu | Leu | Leu | Ser | Val | Gly | Val | Gly | Ile | Tyr | Leu | Leu | Pro | Asn | Arg | |
| | | | 580 | | | | | 585 | | | | | 590 | | |